(12) United States Patent
Kimura et al.

(10) Patent No.: US 6,235,457 B1
(45) Date of Patent: May 22, 2001

(54) ARYLIDENE COMPOUND, AZOMETHINE COMPOUND AND SILVER HALIDE PHOTOGRAPHIC MATERIAL

(75) Inventors: Keizo Kimura; Masashi Ogiyama; Yoshiharu Yabuki; Toshio Kawagishi; Takeshi Nakamine; Yuki Mizukawa, all of Minami-ashigara (JP)

(73) Assignee: Fuji Photo Film Co., Ltd, Kanagawa (JP)

( * ) Notice: Subject to any disclaimer, the term of this patent is extended or adjusted under 35 U.S.C. 154(b) by 0 days.

(21) Appl. No.: 09/499,371

(22) Filed: Feb. 7, 2000

(30) Foreign Application Priority Data

Mar. 25, 1999 (JP) .................................. 11-081889

(51) Int. Cl.$^7$ .............................. G03C 1/83; G03C 1/40; C07F 9/06; C07F 9/28; C07D 293/10
(52) U.S. Cl. .................. 430/522; 430/944; 546/119; 546/120
(58) Field of Search .................... 430/522, 944, 430/580, 591; 546/119, 120

(56) References Cited

U.S. PATENT DOCUMENTS

| | | | | |
|---|---|---|---|---|
| 4,102,688 | * | 7/1978 | Sugiyama et al. | .................. 546/120 |
| 5,063,146 | | 11/1991 | Inagaki et al. | .................. 430/522 |

* cited by examiner

Primary Examiner—Richard L. Schilling

(74) *Attorney, Agent, or Firm*—Birch, Stewart, Kolasch & Birch, LLP

(57) ABSTRACT

An arylidene compound is represented by the formula (I).

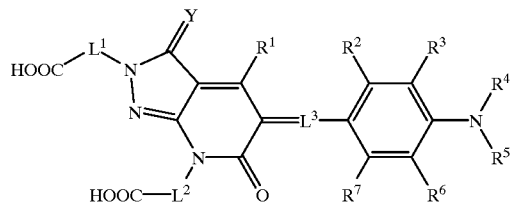

(I)

Each of $L^1$ and $L^2$ independently is a divalent aliphatic group, a divalent aromatic group or a divalent heterocyclic group. $L^3$ is trimethine, pentamethine or heptamethine. Y is $=O$, $=S$ or $=N-R^{10}$. $R^1$ is hydrogen, a halogen atom, cyano, nitro, an aliphatic group, an aromatic group, a heterocyclic group, $-O-R^{11}$, $-S-R^{12}$, $-CO-O-R^{13}$, $-O-CO-R^{14}$, $-NR^{15}R^{16}$, $-CO-NR^{17}R^{18}$, $-SO_2-R^{19}$ or $-SO_2-NR^{20}R^{21}$. Each of $R^2$, $R^3$, $R^6$ and $R^7$ independently is hydrogen, a halogen atom, cyano, an aliphatic group, an aromatic group, $-O-R^{22}$, $-CO-R^{23}$, $-CO-O-R^{24}$, $-NR^{25}R^{26}$, $-NHCO-R^{27}$, $-NH-CO-O-R^{28}$, $-SO_2-R^{29}$ or $-NH-SO_2-R^{30}$. Each of $R^4$ and $R^5$ independently is hydrogen, an aliphatic group, an aromatic group, $-CO-R^{31}$ or $-SO_2-R^{32}$. An azomethine compound and silver halide photographic materials are also disclosed.

20 Claims, No Drawings

ARYLIDENE COMPOUND, AZOMETHINE COMPOUND AND SILVER HALIDE PHOTOGRAPHIC MATERIAL

FIELD OF THE INVENTION

The present invention relates to an arylidene compound and an azomethine compound. The invention also relates to a silver halide photographic material containing an arylidene compound or an azomethine compound as a photographic dye.

BACKGROUND OF THE INVENTION

Arylidene and azomethine compounds are used as dyes for fibers, or are used in paints or silver halide photographic materials.

A dye is added to a silver halide emulsion layer or a non-light-sensitive hydrophilic colloidal layer of the silver halide photographic material to absorb light of a specific wavelength. The dye contained in the silver halide photographic material must satisfy the following conditions (1) to (5).

(1) Appropriate Spectral Absorption

The absorption wavelength region is determined according to use of the dye.

(2) Photographically Chemical Inactivity

The dye should not chemically affect the performance of the photographic material (particularly, of the silver halide emulsion layer). In more detail, the dye must not impair the sensitivity, must not fade the latent image, and must not cause fogging.

(3) Easy Bleach or Removal

The dye functions in principle during imagewise exposure. After exposure, the dye must be bleached or removed from the photographic material. If the dye remains in an obtained image, the image would be colored with the dye. Therefore, the dye should easily be bleached or removed by processing solutions (such as a developing solution, a bleaching solution).

(4) Fast to Diffusion

The dye functions in a specific layer of the photographic material. The dye should not be diffused into other layers. For example, an antihalation dye (should be contained in a non-light-sensitive colloidal layer) diffused in the emulsion layer would degrade the sensitivity of the emulsion layer.

(5) Stability

The color of the dye must not change or fade while the photographic material or a solution of the dye is stored.

It is generally difficult to satisfy the conditions (3) and (4). The dyes satisfying the condition (3), which are easily bleached or removed are also easily diffused into other layers. On the other hand, the dyes satisfying the condition (4), which is hardly diffused are difficult to be bleached or removed.

A silver halide photographic material comprising a dye satisfying the conditions (3) and (4) was proposed. The material contains solid fine particles of the dye having a weak acidic group (e.g., carboxyl). Since the weak acidic group does not dissociate in coating solutions (which are generally acidic or neutral) for preparing the layers of the material, the dye is insoluble in the solutions. Hence, the dye can be incorporated in the form of solid fine particles, which hardly diffuse into other layers. The weak acidic group dissociates in processing solutions (which are generally alkaline), and hence the dye is soluble in the solutions. Accordingly, the dye can be easily removed from the photographic material with the processing solutions.

Japanese Patent Provisional Publications Nos. 3(1991)-7931, 4(1992)-37841, 4(1992)-37842 and 4(1992)-45436 disclose silver halide photographic materials comprising arylidene or azomethine dyes in the form of solid fine particles.

SUMMARY OF THE INVENTION

The applicants have studied the known arylidene and azomethine dyes disclosed in the prior art references. As a result, the inventors note that the dyes need improving in the stability, namely in the condition (5).

An object of the present invention to provide an arylidene compound and an azomethine compound to be used as a stable dye.

Another object of the invention is to provide a silver halide photographic material containing a stable dye. The dye should hardly diffuse and should easily be removed by a processing solution.

The present invention provides an arylidene compound represented by the formula (I):

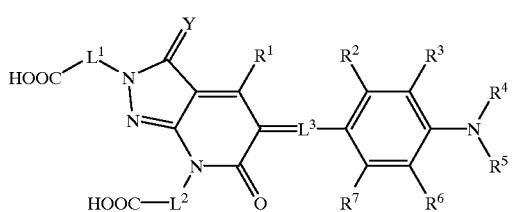

wherein each of $L^1$ and $L^2$ independently is a divalent aliphatic group, a divalent aromatic group or a divalent heterocyclic group; $L^3$ is trimethine, pentamethine or heptamethine; Y is =O, =S or =N—$R^{10}$, in which $R^{10}$ is hydrogen, an aliphatic group, an aromatic group or a heterocyclic group; $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —N$R^{15}R^{16}$, —CO—N$R^{17}R^{18}$, —$SO_2$—$R^{19}$ or —$SO_2$—N$R^{20}R^{21}$, in which each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group; each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —N$R^{25}R^{26}$, —NHCO—$R^{27}$, —NH—CO—O—$R^{28}$, —$SO_2$—$R^{29}$ or —NH—$SO_2$—$R^{30}$, in which each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group; each of $R^4$ and $R^5$ independently is hydrogen, an aliphatic group, an aromatic group, —CO—$R^{31}$ or —$SO_2$—$R^{32}$, in which each of $R^{31}$ and $R^{32}$ independently is an aliphatic group or an aromatic group; and $R^2$ and $R^3$, $R^3$ and $R^4$, $R^4$ and $R^5$, $R^5$ and $R^6$ or $R^6$ and $R^7$ can be combined with each other to form a ring.

The invention also provides a silver halide photographic material comprising a support, a silver halide emulsion layer and a non-light-sensitive hydrophilic colloidal layer, wherein the silver halide emulsion layer or the non-light-sensitive hydrophilic colloidal layer contains an arylidene dye represented by the formula (I).

The invention further provides an azomethine compound represented by the formula (II):

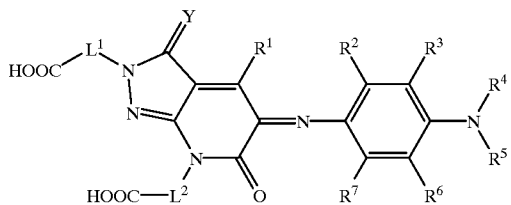

(II)

wherein each of $L^1$ and $L^2$ independently is a divalent aliphatic group, a divalent aromatic group or a divalent heterocyclic group; Y is =O, =S or =N—$R^{10}$, in which $R^{10}$ is hydrogen, an aliphatic group, an aromatic group or a heterocyclic group; $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —NR$^{15}$R$^{16}$, —CO—NR$^{17}$R$^{18}$, —SO2—$R^{19}$ or —SO$_2$—NR$^{20}$R$^{21}$, in which each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group; each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —NR$^{25}$R$^{26}$, —NHCO—$R^{27}$, —NH—CO—O—$R^{28}$, —SO$_2$—$R^{29}$ or —NH—SO$_2$—$R^{30}$, in which each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group; each of $R^4$ and $R^5$ independently is hydrogen, an aliphatic group, an aromatic group, —CO—$R^{31}$ or —SO$_2$—$R^{32}$, in which each of $R^{31}$ and $R^{32}$ independently is an aliphatic group or an aromatic group; and $R^2$ and $R^3$, $R^3$ and $R^4$, $R^4$ and $R^5$, $R^5$ and $R^6$ or $R^6$ and $R^7$ can be combined with each other to form a ring.

The invention furthermore provides a silver halide photographic material comprising a support, a silver halide emulsion layer and a non-light-sensitive hydrophilic colloidal layer, wherein the silver halide emulsion layer or the non-light-sensitive hydrophilic colloidal layer contains an azomethine dye represented by the formula (II).

DETAILED DESCRIPTION OF THE INVENTION

The arylidene compound is represented by the formula (I).

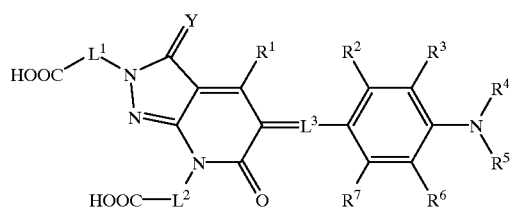

(I)

In the formula (I), each of $L^1$ and $L^2$ independently is a divalent aliphatic group, a divalent aromatic group or a divalent heterocyclic group.

Each of $L^1$ and $L^2$ preferably is a divalent aliphatic group or a divalent aromatic group, and more preferably is a divalent aromatic group.

The divalent aliphatic group means an alkylene group, a substituted alkylene group, an alkenylene group, a substituted alkenylene group, an alkynylene group or a substituted alkynylene group.

The alkylene group can have a branched structure. The alkylene group preferably has 1 to 20 carbon atoms, and more preferably has 1 to 18 carbon atoms.

The alkylene moiety of the substituted alkylene group is the same as the above-described alkylene group.

The alkenylene group can have a branched structure. The alkenylene group preferably has 2 to 20 carbon atoms, and more preferably has 2 to 18 carbon atoms.

The alkenylene moiety of the substituted alkenylene group is the same as the above-described alkenylene group.

The alkynylene group can have a branched structure. The alkynylene group preferably has 2 to 20 carbon atoms, and more preferably has 2 to 18 carbon atoms.

The alkynylene moiety of the substituted alkynylene group is the same as the above-described alkynylene group.

Examples of the substituent groups of the substituted alkylene, alkenylene and alkynylene groups include a halogen atom, cyano, nitro, an aromatic group, a heterocyclic group, —O—$R^{33}$, —S—$R^{34}$, —CO—O—$R^{35}$, —NR$^{36}$R$^{37}$, —CO—NR$^{38}$R$^{39}$, —SO$_2$—$R^{40}$ or —SO$_2$—NR$^{41}$R$^{42}$. Each of $R^{33}$, $R^{34}$, $R^{35}$, $R^{36}$, $R^{37}$, $R^{38}$, $R^{39}$, $R^{40}$, $R^{41}$ and $R^{42}$ independently is hydrogen, an aliphatic group or an aromatic group. The aliphatic, aromatic and heterocyclic groups are described below in the definition of $R^1$.

The divalent aromatic group means an arylene group or a substituted arylene group.

The arylene group preferably is phenylene or naphthylene, more preferably is phenylene, and most preferably is p-phenylene.

The arylene moiety of the substituted arylene group is the same as the above-described arylene group.

Examples of the substituent groups of the substituted arylene groups include a halogen atom, cyano, nitro, an aromatic group, a heterocyclic group, —O—$R^{43}$, —S—$R^{44}$, —CO—O—$R^{45}$, —NR$^{46}$R$^{47}$, —CO—NR$^{48}$R$^{49}$, —SO$_2$—$R^{50}$ or —SO$_2$—NR$^{51}$R$^{52}$. Each of $R^{43}$, $R^{44}$, $R^{45}$, $R^{46}$, $R^{47}$, $R^{48}$, $R^{49}$, $R^{50}$, $R^{51}$ and $R^{52}$ independently is hydrogen, an aliphatic group or an aromatic group. The aliphatic, aromatic and heterocyclic groups are described below in the definition of $R^1$.

The divalent heterocyclic group preferably comprises a 5-membered or 6-membered saturated or unsaturated heterocyclic ring. The heterocyclic ring can be condensed with an aliphatic ring, an aromatic ring or another heterocyclic ring. Examples of the hetero atom in the heterocyclic rings include B, N, O, S, Se and Te. The hetero atoms preferably include N, O or S. The heterocyclic ring preferably has at least two carbon atoms having free monovalences. In other words, the divalent heterocyclic group preferably connects at the two carbon atoms. Examples of the saturated heterocyclic ring include pyrrolidine ring, morpholine ring, 2-bora-1,3-dioxolane ring and 1,3-thiazolidine ring. Examples of the unsaturated heterocyclic ring include imidazole ring, thiazole ring, benzothiazole ring, benzoxazole ring, benzotriazole ring, benzoselenazole ring, pyridine ring, pyrimidine ring and quinoline ring.

The divalent heterocyclic group can have a substituent. Examples of the substituent include a halogen atom, cyano, nitro, an aliphatic group, an aromatic group, a heterocyclic group, —O—$R^{53}$, —S—$R^{54}$, —CO—O—$R^{55}$, —NR$^{56}$R$^{57}$, —CO—NR$^{58}$R$^{59}$, —SO$_2$—$R^{60}$ or —SO$_2$—NR$^{61}$R$^{62}$. Each of $R^{53}$, $R^{54}$, $R^{55}$, $R^{56}$, $R^{57}$, $R^{58}$, $R^{59}$, $R^{60}$, $R^{61}$ and $R^{62}$ independently is hydrogen, an aliphatic group or an aromatic group. The aliphatic, aromatic and heterocyclic groups are described below in the definition of $R^1$.

In the formula (I), $L^3$ is trimethine, pentamethine or heptamethine.

$L^3$ Preferably is trimethine or pentamethine, and more preferably is trimethine.

The methines can have substituent groups. In the case that methines has only one substituent group, the substituent group is preferably attached to the centered methine (the meso-position). Further, two substituent groups can be combined to form a 5-membered or 6-membered unsaturated aliphatic ring (e.g., cyclopentene ring, cyclohexene ring). Examples of the substituent groups include a halogen atom, cyano, nitro, an aliphatic group, an aromatic group, a heterocyclic group, $—O—R^{63}$, $—S—R^{64}$, $—CO—R^{65}$, $—CO—O—R^{66}$, $—NR^{67}R^{68}$, $—CO—NR^{69}R^{70}$, $—NH—CO—R^{71}$, $—NH—CO—NH—R^{72}$, $—NH—CO—O—R^{73}$, $—SO_2—R^{74}$, $—SO_2—NR^{75}R^{76}$, $—NH—SO_2—R^{77}$, $—CO—NH—SO_2—R^{78}$ or $—SO_2—NH—CO—R^{79}$. Each of $R^{63}$, $R^{64}$, $R^{65}$, $R^{66}$, $R^{67}$ $R^{68}$ $R^{69}$, $R^{70}$, $R^{71}$, $R^{72}$, $R^{73}$, $R^{74}$, $R^{75}$, $R^{76}$, $R^{77}$, $R^{78}$ and $R^{79}$ independently is hydrogen, an aliphatic group or an aromatic group. The aliphatic, aromatic and heterocyclic groups are described below in the definition of $R^1$.

In the formula (I), Y is $=O$, $=S$ or $=N—R^{10}$. $R^{10}$ is hydrogen, an aliphatic group, an aromatic group or a heterocyclic group. The aliphatic, aromatic and heterocyclic groups are described below in the definition of $R^1$.

Y preferably is $=O$.

In the formula (I), $R^1$ is hydrogen, a halogen atom, cyano, nitro, an aliphatic group, an aromatic group, a heterocyclic group, $—O—R^{11}$, $—S—R^{12}$, $—CO—O—R^{13}$, $—O—CO—R^{14}$, $—NR^{15}R^{16}$, $—CO—NR^{17}R^{18}$, $—SO_2—R^{19}$ or $—SO_2—NR^{20}R^{21}$. Each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group.

$R^1$ preferably is hydrogen, an aliphatic group, an aromatic group, $—O—R^{11}$, $—CO—O—R^{13}$ or $—CO—NR^{17}R^{18}$, more preferably is hydrogen, an alkyl group, a substituted alkyl group, an aryl group or a substituted aryl group, further preferably is hydrogen, an alkyl group having 1 to 10 carbon atoms, a substituted alkyl group having 1 to 10 carbon atoms, an aryl group having 6 to 10 carbon atoms or a substituted aryl group having 6 to 10 carbon atoms, and most preferably is hydrogen, an alkyl group having 1 to 4 carbon atoms, a substituted alkyl group having 1 to 4 carbon atoms, phenyl or a substituted phenyl group having 6 to 10 carbon atoms.

In the present specification, "an aliphatic group" means an alkyl group, a substituted alkyl group, an alkenyl group, a substituted alkenyl group, an alkynyl group, a substituted alkynyl group, an aralkyl group or a substituted aralkyl group.

The alkyl group can have a branched structure. The alkyl group preferably has 1 to 20 carbon atoms, and more preferably has 1 to 18 carbon atoms.

The alkyl moiety of the substituted alkyl group is the same as the above-described alkyl group.

The alkenyl group can have a branched structure. The alkenyl group preferably has 2 to 20 carbon atoms, and more preferably has 2 to 18 carbon atoms.

The alkenyl moiety of the substituted alkenyl group is the same as the above-described alkenyl group.

The alkynyl group can have a branched structure. The alkynyl group preferably has 2 to 20 carbon atoms, and more preferably has 2 to 18 carbon atoms. The alkynyl moiety of the substituted alkynyl group is the same as the above-described alkynyl group.

The alkyl moiety of the aralkyl group and the substituted aralkyl group is the same as the above-described alkyl group. The aryl moiety of the aralkyl group and the substituted aralkyl group is the same as the below-described aryl group.

Examples of the substituent groups of the substituted alkyl group, the substituted alkenyl group, the substituted alkynyl group and the alkyl moiety of the substituted aralkyl group include a halogen atom, cyano, nitro, a heterocyclic group, $—O—R^{80}$, $—S—R^{81}$, $—CO—O—R^{82}$, $—NR^{83}R^{84}$, $—CO—NR^{85}R^{86}$, $—SO_2—R^{87}$ or $—SO_2—NR^{88}R^{89}$. Each of $R^{80}$, $R^{81}$, $R^{82}$, $R^{83}$, $R^{84}$, $R^{85}$, $R^{86}$, $R^{87}$, $R^{88}$ and $R^{89}$ independently is hydrogen, an aliphatic group or an aromatic group.

Examples of the substituent groups of the aryl moiety of the substituted aralkyl group are the same as those of the substituent groups in the substituted aryl group described below.

In the present specification, "an aromatic group" means an aryl group or a substituted aryl group.

The aryl group preferably is phenyl or naphthyl, and more preferably is phenyl.

The aryl moiety of the substituted aryl group is the same as the above-described aryl group.

Examples of the substituent groups of the substituted aryl group include a halogen atom, cyano, nitro, an aliphatic group, a heterocyclic group, $—O—R^{90}$, $—S—R^{91}$, $—CO—O—R^{92}$, $—NR^{93}R^{94}$, $—CO—NR^{95}R^{96}$, $—SO_2—R^{97}$ or $—SO_2—NR^{98}R^{99}$. Each of $R^{90}$, $R^{91}$, $R^{92}$, $R^{93}$, $R^{94}$, $R^{95}$, $R^{96}$, $R^{97}$, $R^{98}$ and $R^{99}$ independently is hydrogen, an aliphatic group or an aromatic group.

The heterocyclic group in the present specification preferably comprises a 5-membered or 6-membered saturated or unsaturated heterocyclic ring. The heterocyclic ring can be condensed with an aliphatic ring, an aromatic ring or another heterocyclic ring. Examples of the hetero atoms in the heterocyclic ring include B, N, O, S, Se and Te. The hetero atoms preferably include N, O or S. The heterocyclic ring preferably has at least two carbon atoms having free monovalences. In other words, the divalent heterocyclic group preferably connects at the two carbon atoms. Examples of the saturated heterocyclic ring include pyrrolidine ring, morpholine ring, 2-bora-1,3-dioxolane ring and 1,3-thiazolidine ring. Examples of the unsaturated heterocyclic ring include imidazole ring, thiazole ring, benzothiazole ring, benzoxazole ring, benzotriazole ring, benzoselenazole ring, pyridine ring, pyrimidine ring and quinoline ring.

The heterocyclic group can have a substituent group. Examples of the substituent groups include a halogen atom, cyano, nitro, an aliphatic group, an aromatic group, a heterocyclic group, $—O—R^{100}$, $—S—R^{101}$, $—CO—O—R^{102}$, $—NR^{103}R^{104}$, $—CO—NR^{105}R^{106}$, $—SO_2—R^{107}$ or $—SO_2—NR^{108}R^{109}$. Each of $R^{100}$, $R^{101}$, $R^{102}$, $R^{103}$, $R^{104}$, $R^{105}$, $R^{106}$, $R^{107}$, $R^{108}$ and $R^{109}$ independently is hydrogen, an aliphatic group or an aromatic group.

In the formula (I), each of $R^2$, $R^3$, $R^6$ and $R^7$ independently is hydrogen, a halogen atom, cyano, an aliphatic group, an aromatic group, $—O—R^{22}$, $—CO—R^{23}$, $—CO—O—R^{24}$, $—NR^{25}R^{26}$, $—NHCO—R^{27}$, $—NH—CO—O—R^{28}$, $—SO_2—R^{29}$ or $—NH—SO_2—R^{30}$. Each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group.

Each of $R^2$ and $R^7$ preferably is hydrogen, a halogen atom, an aliphatic group or —O—$R^{22}$, more preferably is hydrogen, chlorine, fluorine, an alkyl group, a substituted alkyl group, an alkoxy group or a substituted alkoxy group, further preferably is hydrogen, chlorine, fluorine, an alkyl group having 1 to 10 carbon atoms, a substituted alkyl group having 1 to 10 carbon atoms, an alkoxy group having 1 to 10 carbon atoms or a substituted alkoxy group having 1 to 10 carbon atoms, and most preferably is hydrogen, an alkyl group having 1 to 5 carbon atoms or an alkoxy group having 1 to 8 carbon atoms.

Each of $R^3$ and $R^6$ preferably is hydrogen or an aliphatic group, more preferably is hydrogen or an alkyl group, further preferably is hydrogen or an alkyl group having 1 to 8 carbon atoms, and most preferably is hydrogen.

In the formula (I), each of $R^4$ and $R^5$ independently is hydrogen, an aliphatic group, an aromatic group, —CO—$R^{31}$ or —SO$_2$—$R^{32}$. Each of $R^{31}$ and $R^{32}$ independently is an aliphatic group or an aromatic group.

Each of $R^4$ and $R^5$ preferably is hydrogen, an aliphatic group or an aromatic group, more preferably is hydrogen, an alkyl group or an aryl group, further preferably is hydrogen or an alkyl group, and most preferably is hydrogen or an alkyl group having 1 to 18 carbon atoms.

In the formula (I), $R^2$ and $R^3$, $R^3$ and $R^4$, $R^4$ and $R^5$, $R^5$ and $R^6$ or $R^6$ and $R^7$ can be combined with each other to form a ring. $R^3$ and $R^4$ or $R^5$ and $R^6$ preferably forms a ring.

The ring made of $R^2$ and $R^3$ or $R^6$ and $R^7$ preferably is a 5-membered or 6-membered ring. The ring preferably is an aromatic ring (e.g., benzene ring) or an unsaturated heterocyclic ring (e.g., pyridine ring, imidazole ring, thiazole ring, pyrimidine ring).

The ring made of $R^3$ and $R^4$ or $R^5$ and $R^6$ preferably is a 5-membered or 6-membered ring. Examples of the rings include tetrahydroquinoline ring and dihydroindole ring.

The ring made of $R^4$ and $R^5$ preferably is a 5-membered or 6-membered ring. Examples of the rings include pyrrolidine ring, piperidine ring and morpholine ring.

The azomethine compound is represented by the formula (II):

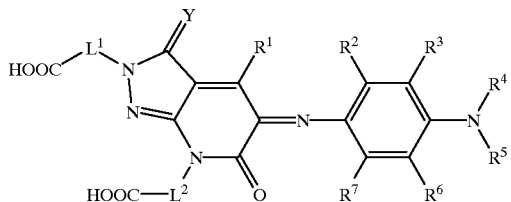

(II)

In the formula (II), each of $L^1$ and $L^2$ independently is a divalent aliphatic group, a divalent aromatic group or a divalent heterocyclic group.

Each of $L^1$ and $L^2$ preferably is a divalent aliphatic group or a divalent aromatic group, and more preferably is a divalent aromatic group.

Examples and definitions of the divalent aliphatic group, the divalent aromatic group and the divalent heterocyclic group are the same as those in the formula (I) described above.

In the formula (II), Y is =O, =S, or =N—$R^{10}$. $R^{10}$ is hydrogen, an aliphatic group, an aromatic group or a heterocyclic group.

Y preferably is =O.

In the formula (II), $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —NR$^{15}$R$^{16}$, —CO—NR$^{17}$R$^{18}$, —SO$_2$—$R^{19}$ or —SO$_2$—NR$^{20}$R$^{21}$. Each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group.

$R^1$ preferably is hydrogen, an aliphatic group, an aromatic group, —O—$R^{11}$, —CO—O—$R^{13}$ or —CO—NR$^{17}$R$^{18}$, more preferably is hydrogen, an alkyl group, a substituted alkyl group, an aryl group or a substituted aryl group, further preferably is hydrogen, an alkyl group having 1 to 10 carbon atoms, a substituted alkyl group having 1 to 10 carbon atoms, an aryl group having 6 to 10 carbon atoms or a substituted aryl group having 6 to 10 carbon atoms, and most preferably is hydrogen, an alkyl group having 1 to 4 carbon atoms, a substituted alkyl group having 1 to 4 carbon atoms, phenyl or a substituted phenyl group having 6 to 10 carbon atoms.

In the formula (II), each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —NR$^{25}$R$^{26}$, —NHCO—$R^{27}$, —NH—CO—O—$R^{28}$, —SO$_2$—$R^{29}$ or —NH—SO$_2$—$R^{30}$. Each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group.

Each of $R^2$ and $R^7$ preferably is hydrogen, a halogen atom, an aliphatic group or —O—$R^{22}$, more preferably is hydrogen, chlorine, fluorine, an alkyl group, a substituted alkyl group, an alkoxy group or a substituted alkoxy group, further preferably is hydrogen, chlorine, fluorine, an alkyl group having 1 to 10 carbon atoms, a substituted alkyl group having 1 to 10 carbon atoms, an alkoxy group having 1 to 10 carbon atoms or a substituted alkoxy group having 1 to 10 carbon atoms, and most preferably is hydrogen, an alkyl group having 1 to 5 carbon atoms or an alkoxy group having 1 to 8 carbon atoms.

Each of $R^3$ and $R^6$ preferably is hydrogen or an aliphatic group, more preferably is hydrogen or an alkyl group, further preferably is hydrogen or an alkyl group having 1 to 8 carbon atoms, and most preferably is hydrogen.

In the formula (II), each of $R^4$ and $R^5$ independently is hydrogen, an aliphatic group, an aromatic group, —CO—$R^{31}$ or —SO$_2$—$R^{32}$. Each of $R^{31}$ and $R^{32}$ independently is an aliphatic group or an aromatic group.

Each of $R^4$ and $R^5$ preferably is hydrogen, an aliphatic group or an aromatic group, more preferably is hydrogen, an alkyl group or an aryl group, further preferably is hydrogen or an alkyl group, and most preferably is hydrogen or an alkyl group having 1 to 18 carbon atoms.

In the formula (II), $R^2$ and $R^3$, $R^3$ and $R^4$, $R^4$ and $R^5$, $R^5$ and $R^6$ or $R^6$ and $R^7$ can be combined with each other to form a ring. $R^3$ and $R^4$ or $R^5$ and $R^6$ preferably forms a ring.

Examples and definition of the ring are the same as those of the ring in the formula (I) described above.

Examples of the arylidene compound represented by the formula (I) and the azomethine compound represented by the formula (II) are shown below.

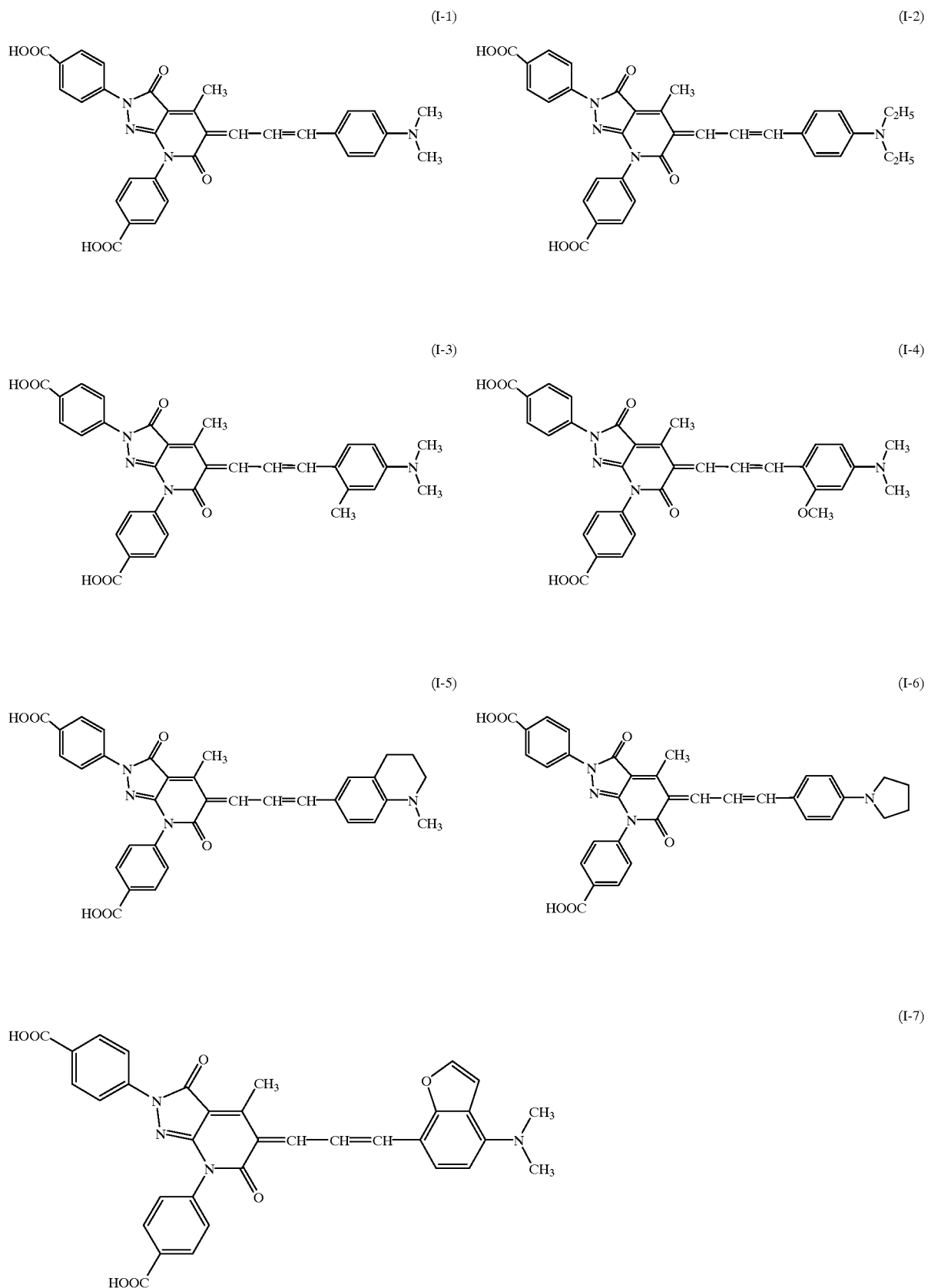

-continued
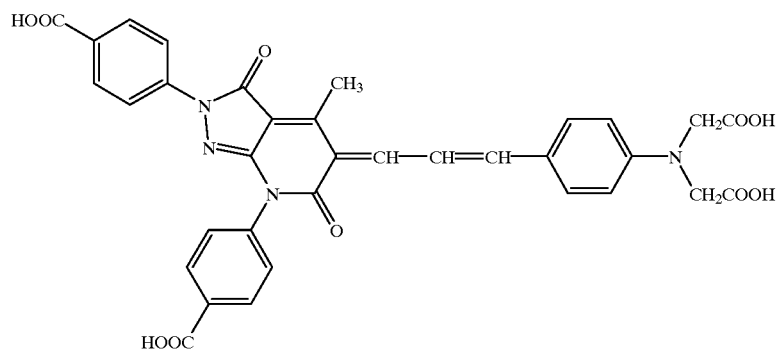
(I-8)
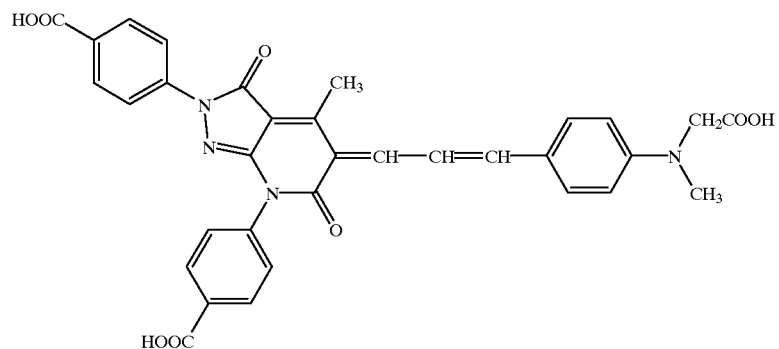
(I-9)
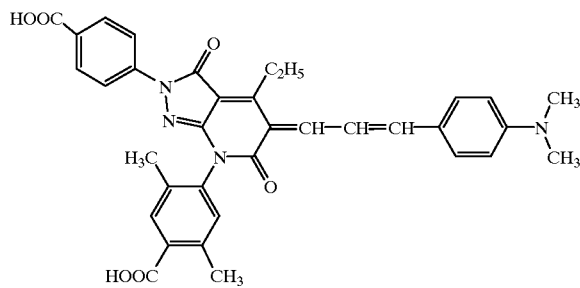
(I-10)
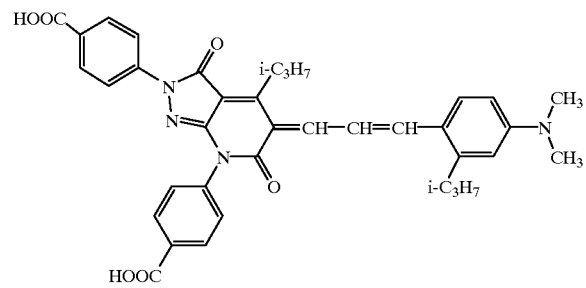
(I-11)
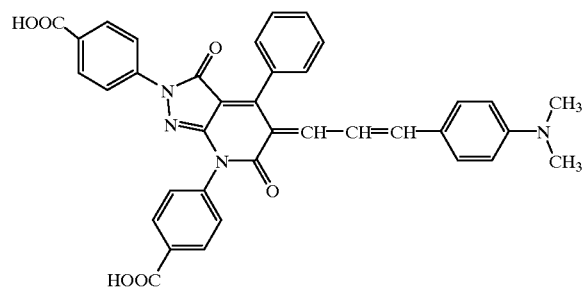
(I-12)
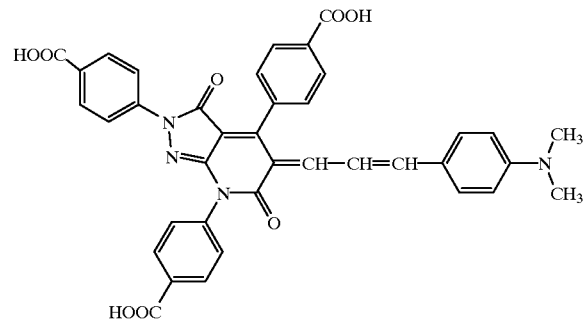
(I-13)

-continued
(I-14)
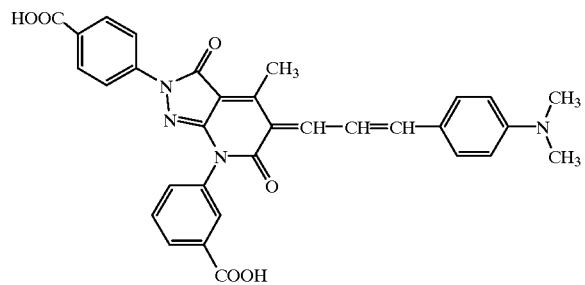
(I-15)
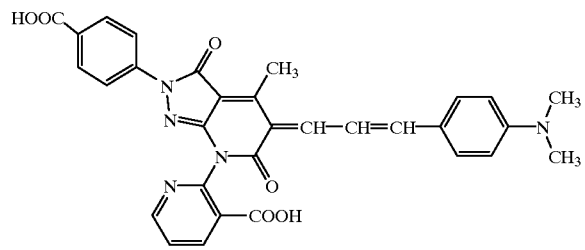
(I-16)
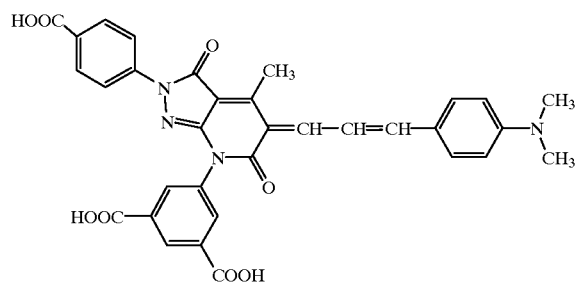
(I-17)
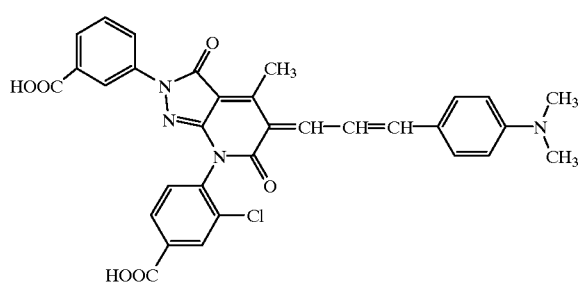
(I-18)
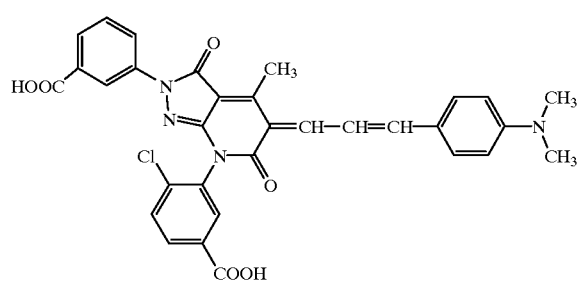
(I-19)
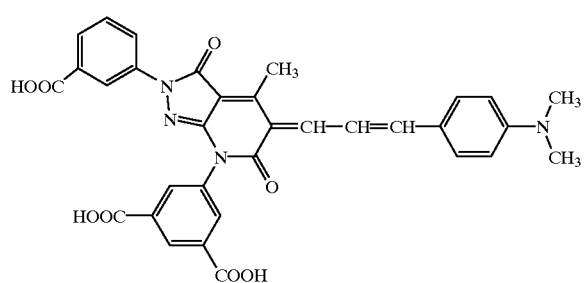
(I-20)
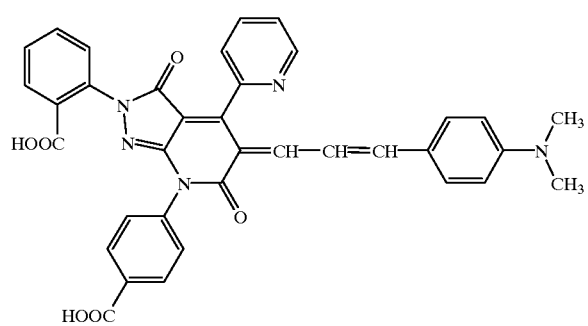
(I-21)
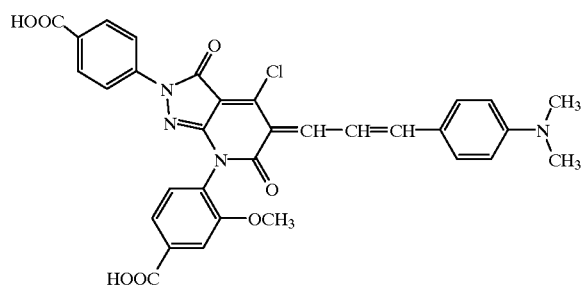
(I-22)
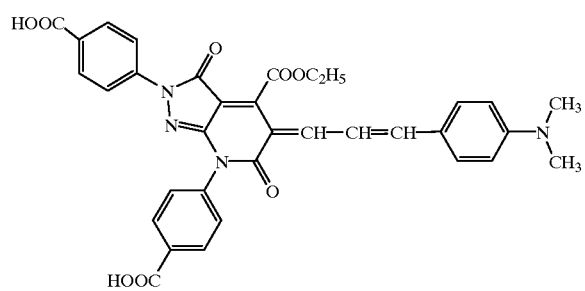
(I-23)
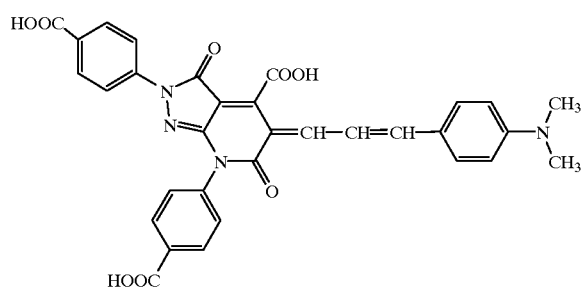

-continued
(I-24)
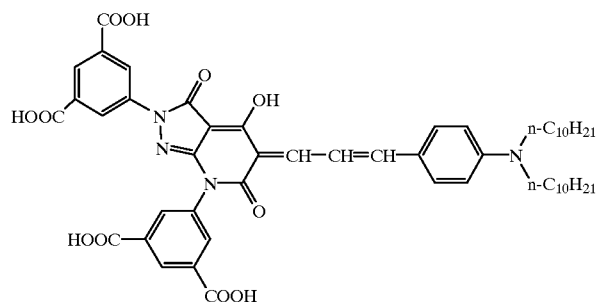
(I-25)
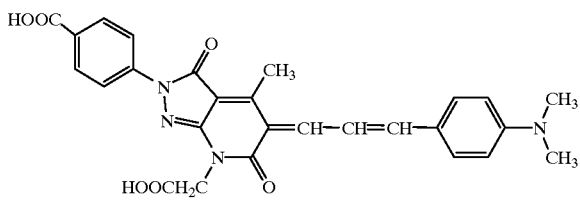
(I-26)
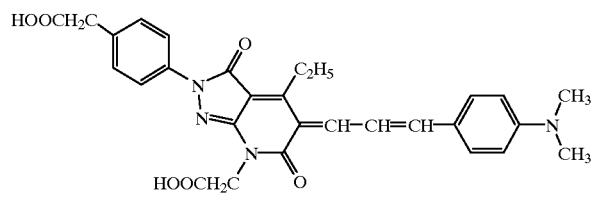
(I-27)
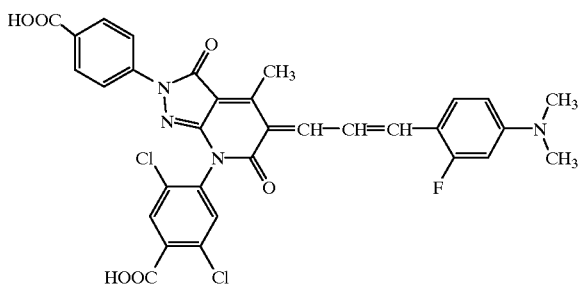
(I-28)
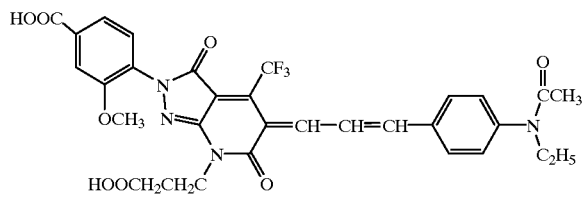
(I-29)
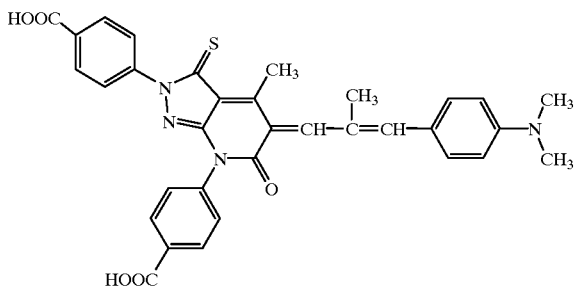
(I-30)
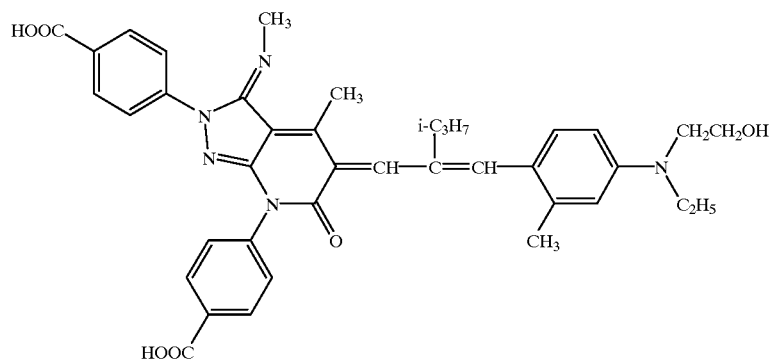

(I-31)
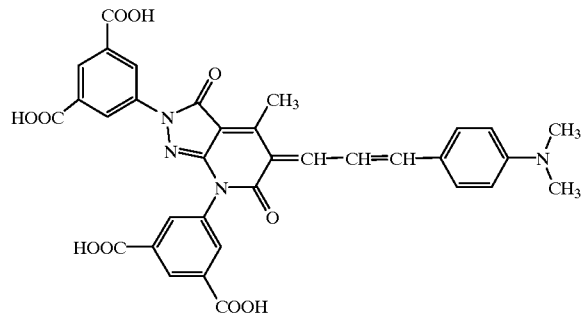
(I-32)
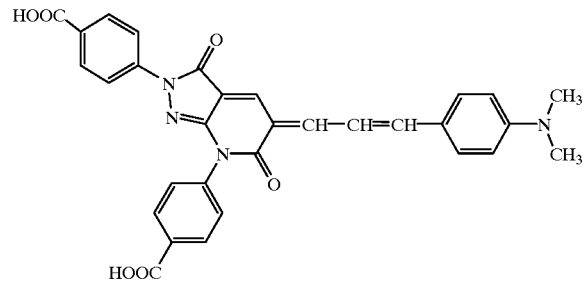
(I-33)
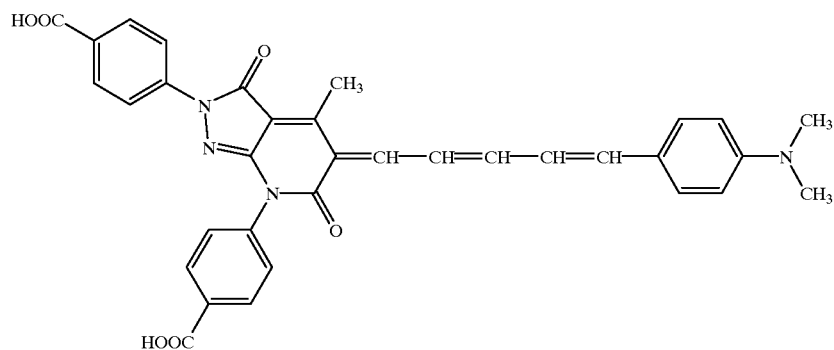
(I-34)
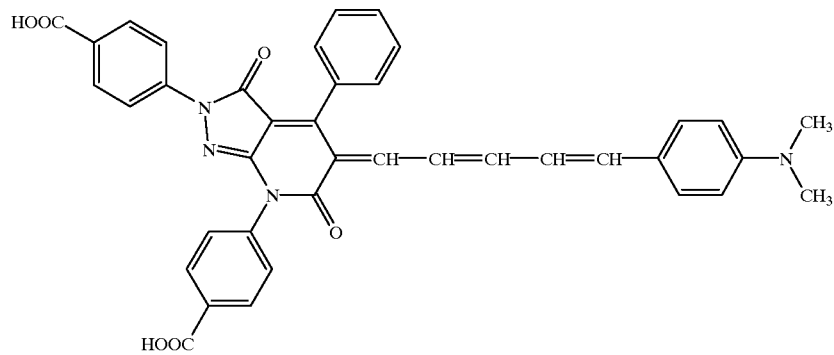
(I-35)
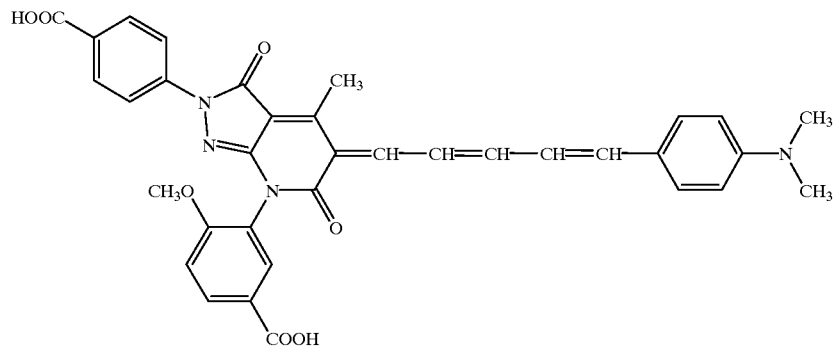

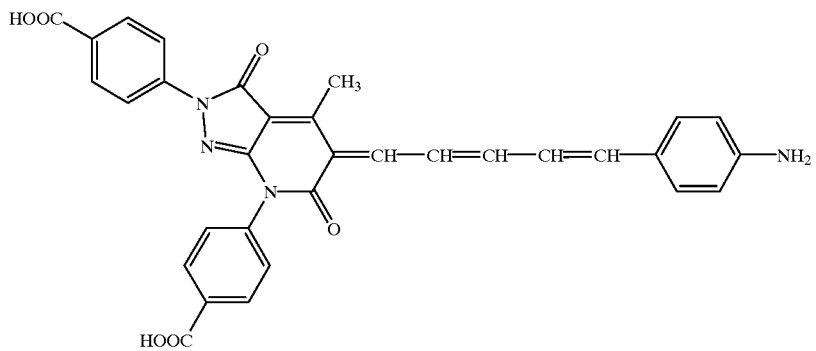
(I-36)
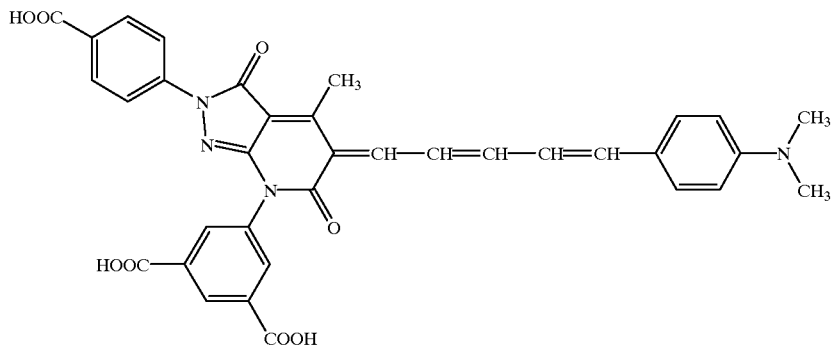
(I-37)
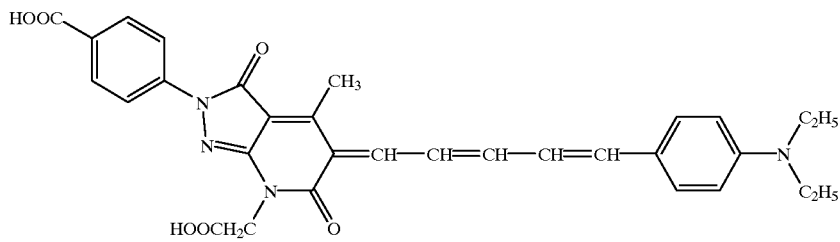
(I-38)
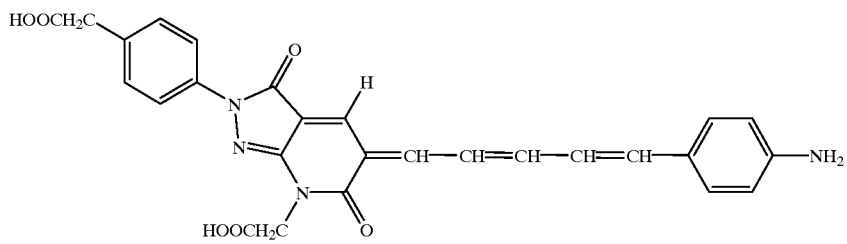
(I-39)
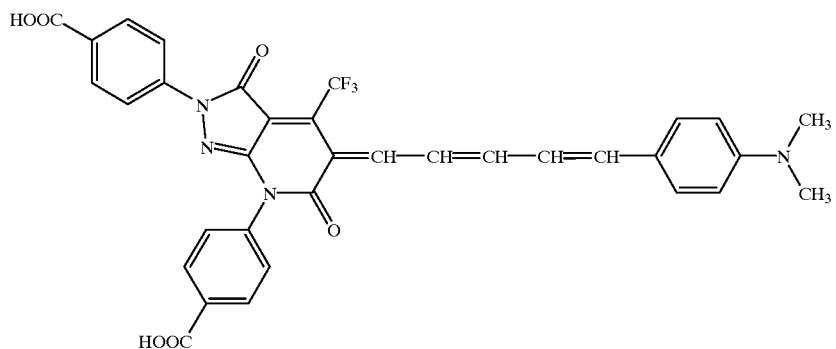
(I-40)

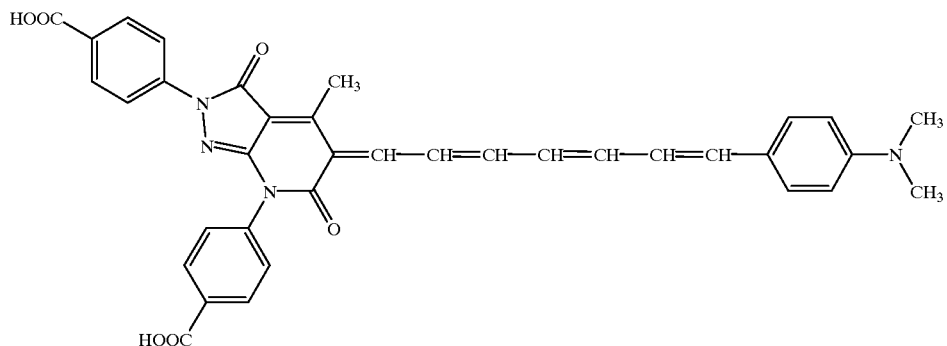
(I-41)
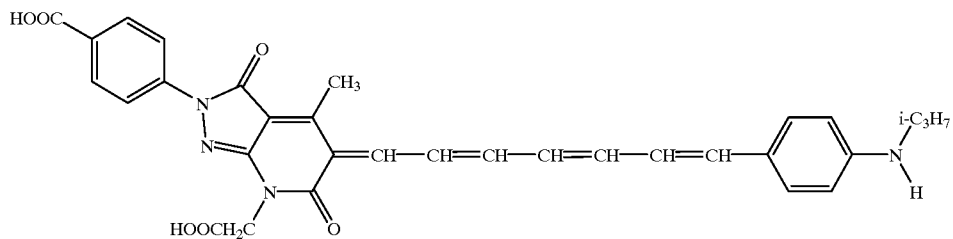
(I-42)
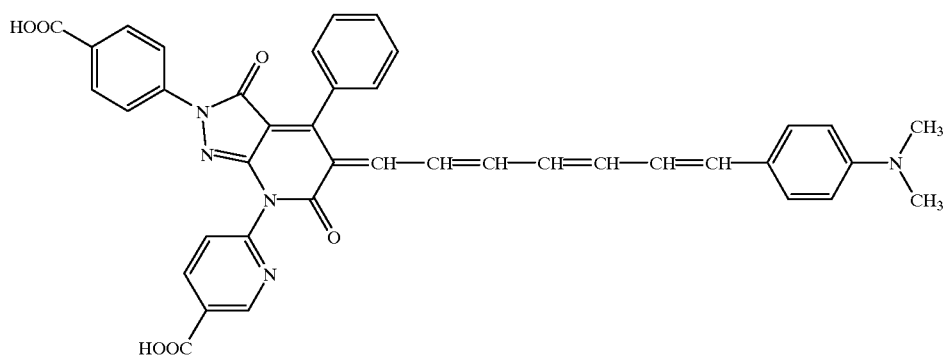
(I-43)
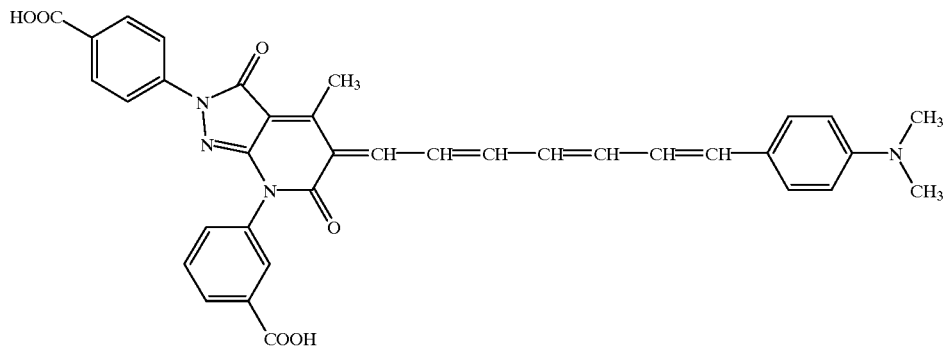
(I-44)

-continued
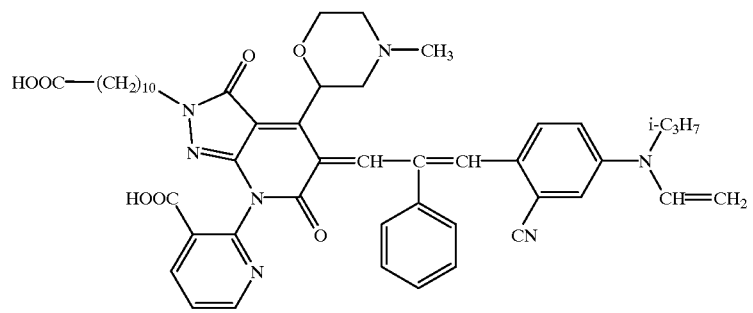
(I-45)
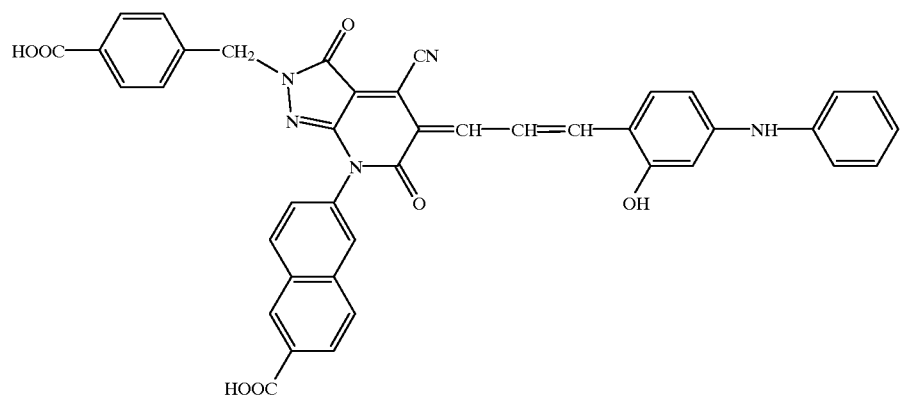
(I-46)
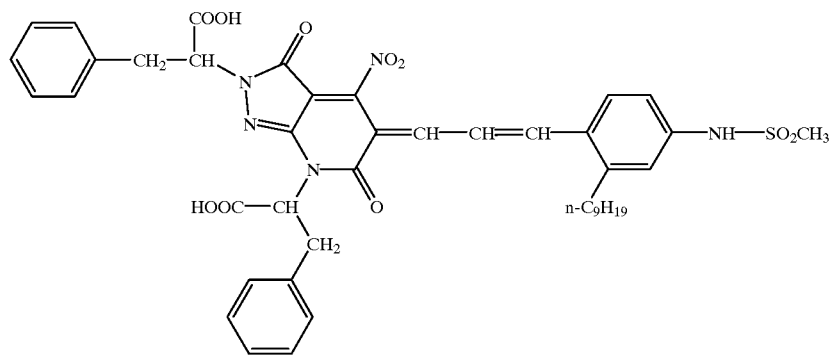
(I-47)
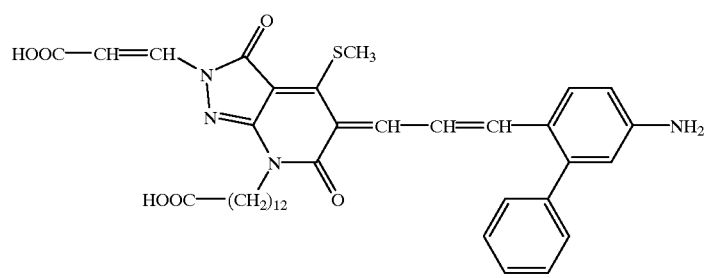
(I-48)

-continued
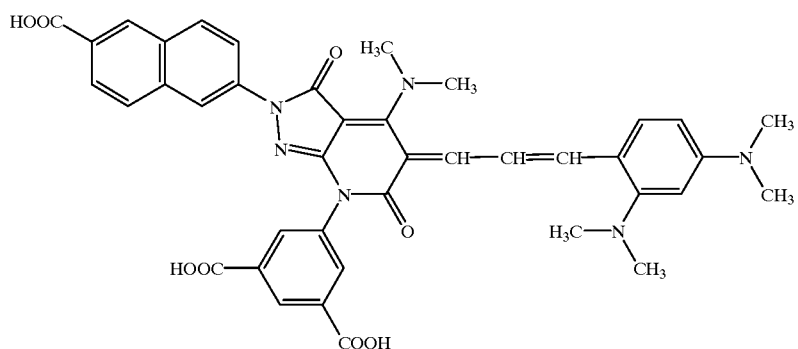
(I-49)
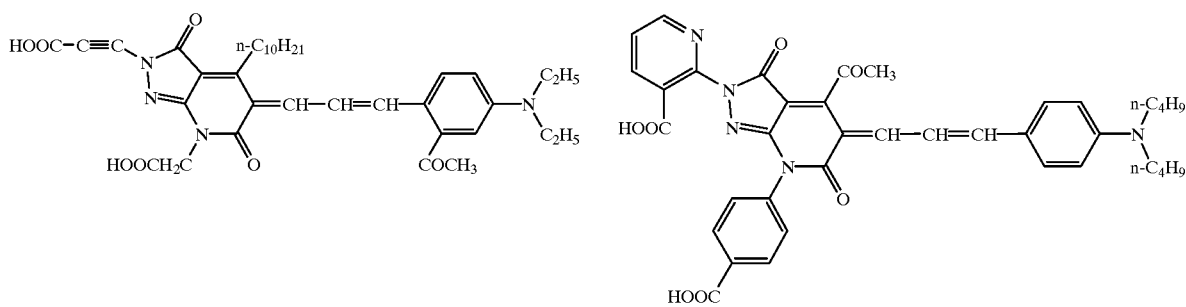
(I-50) (I-51)
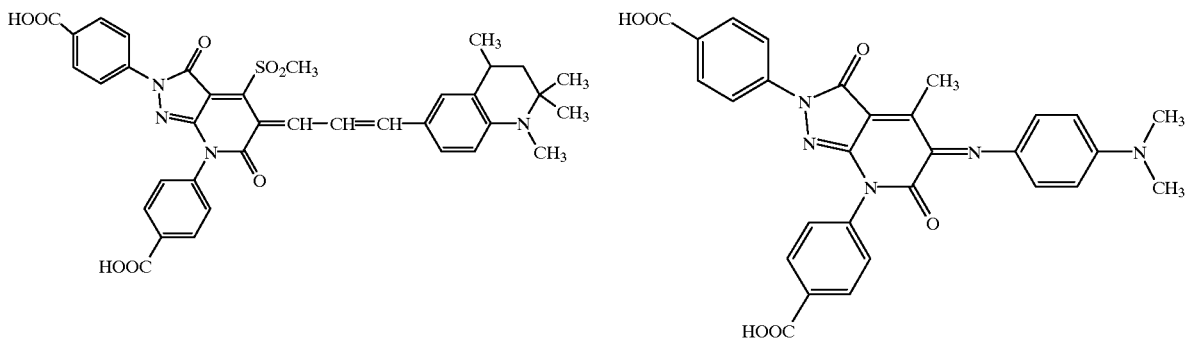
(I-52) (II-1)
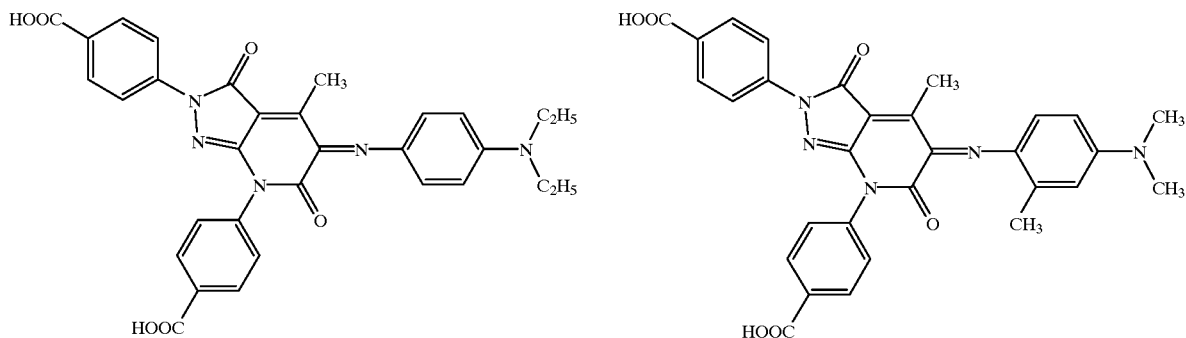
(II-2) (II-3)

-continued
(II-4)
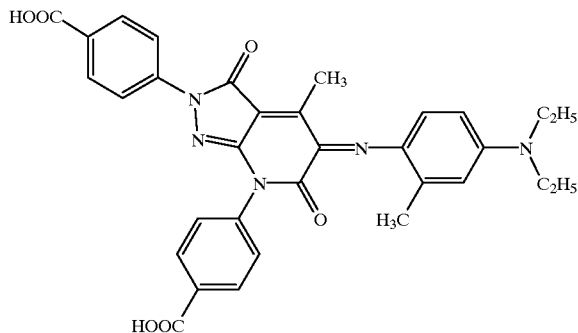
(II-5)
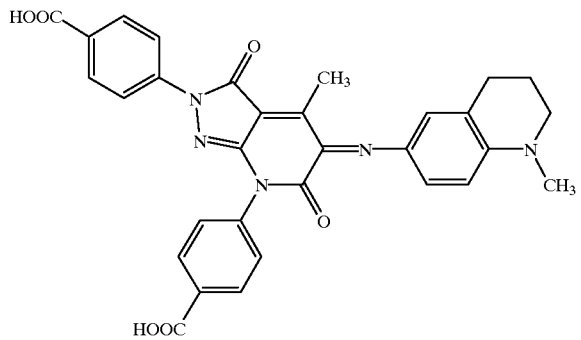
(II-6)
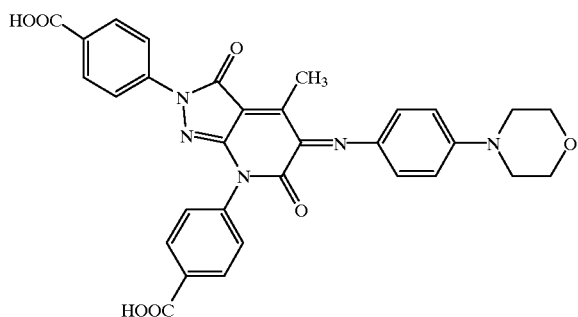
(II-7)
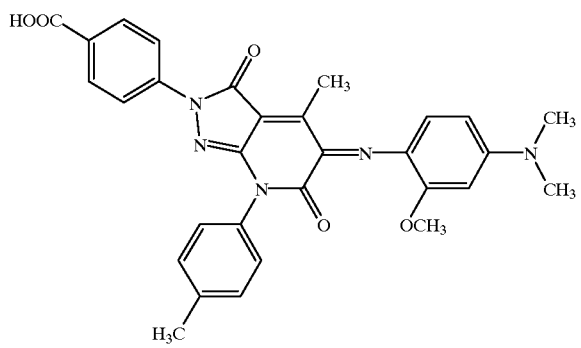
(II-8)
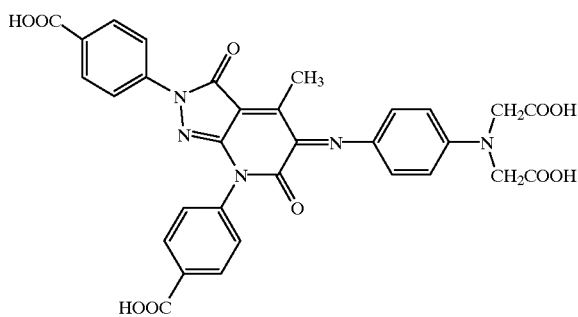
(II-9)
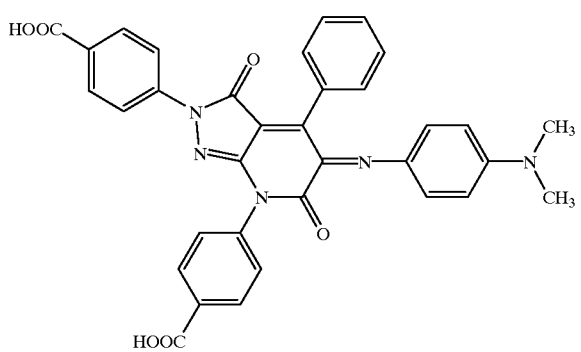
(II-10)
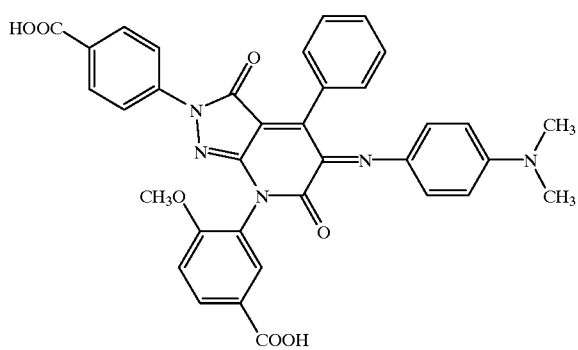
(II-11)
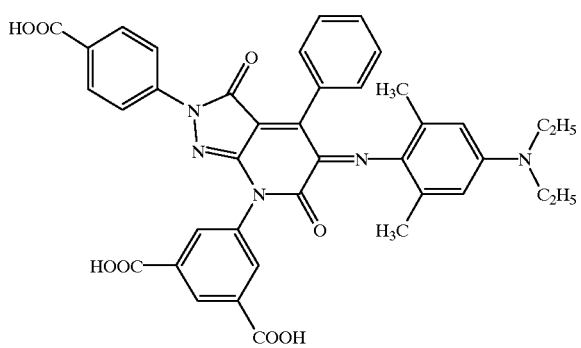

-continued
(II-12)
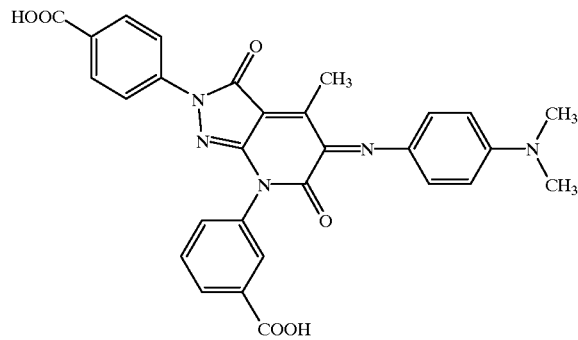
(II-13)
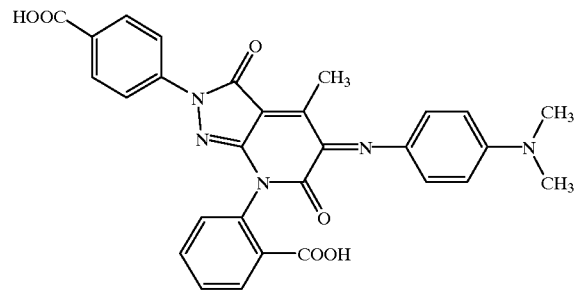
(II-14)
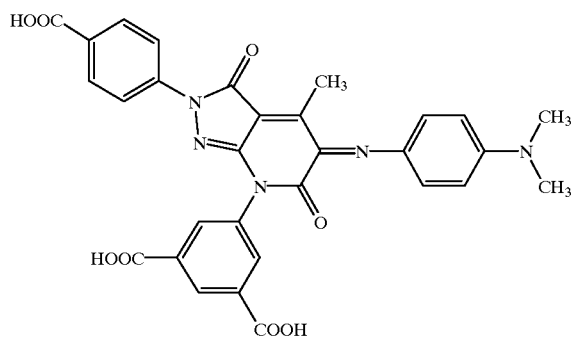
(II-15)
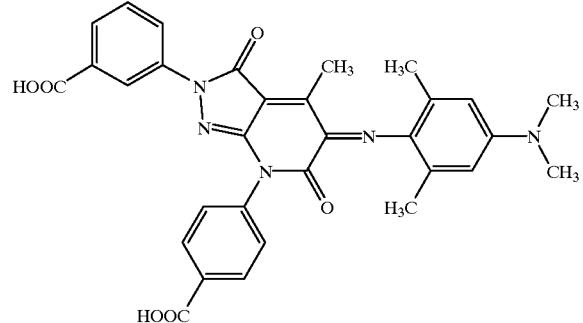
(II-16)
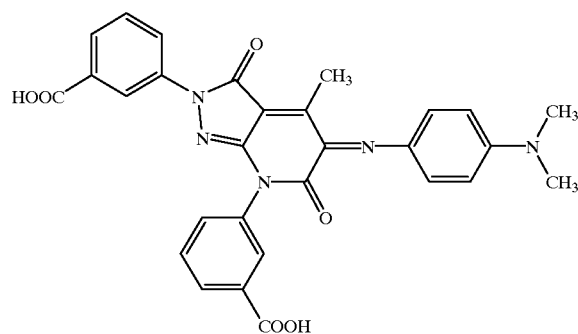
(II-17)
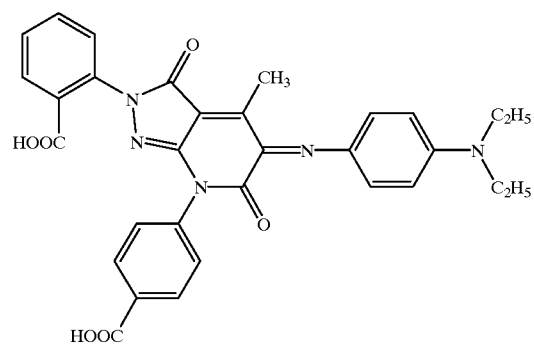
(II-18)
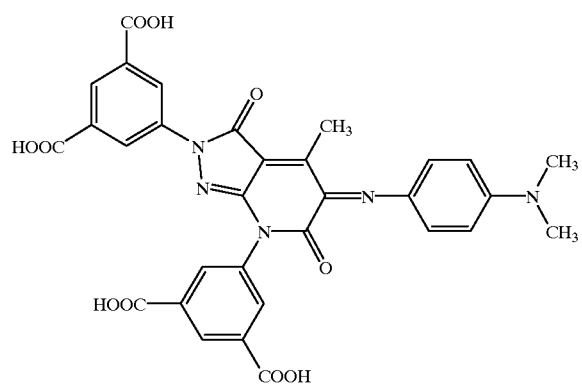
(II-19)
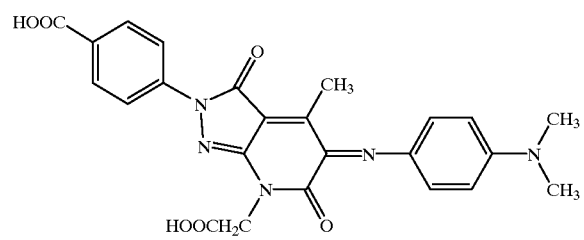

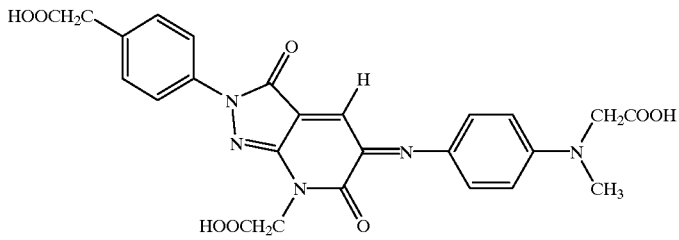

(II-20)

The arylidene compounds and the azomethine compounds can be synthesized by referring to the descriptions of Japanese Patent Provisional Publications Nos. 52(1977)-135335 and 3(1991)-7931.

When the arylidene or azomethine compounds are used as dyes, they are preferably in the form of solid fine particles dispersed in a medium. Examples of the dispersing media include water and alcohols. The dye dispersion can be mechanically prepared by using a dispersing machine such as a ball mill, a vibrating ball mill, a planetary ball mill, a sand mill, a colloid mill, a jet mill or a roll mill. Further, a dispersing agent can also be used. In that case, the dye is dissolved in an appropriate solvent with the dispersing agent, and then a poor solvent for the dye is added to deposit fine crystalline precipitate of the dye. The fine crystals of the dye can be also obtained by the steps of dissolving the dye in a solvent having a proper pH value and adjusting the pH value to deposit the crystals.

A proper binder is added to the dye dispersion to prepare a coating solution for the layer containing the dye. The layer can be also formed from a coating solution dissolving a salt of the dye, and then acidified to deposit the solid fine particles of the dye. In this case, the acidification degree depends on the pKa of the dissociative group (i.e., carboxyl) of the dye. The layer can be acidified beforehand by undercoating with an acidic material or by applying the acidic material on the layer.

As the binder for the layer containing the dye, hydrophilic natural or synthesized polymers are preferably used.

The natural polymers are proteins and polysaccharides. Examples of the proteins include gelatin, albumin, casein, and derivatives thereof. Examples of the gelatin derivatives include graft polymer of gelatin. Examples of the polysaccharides include cellulose, dextrin, sodium alginate, pectin, starch, gum arabic, and derivatives thereof. Examples of the cellulose derivatives include hydroxyethyl cellulose, hydroxymethyl cellulose, hydroxypropyl cellulose, carboxylmethyl cellulose, ethyl cellulose, methyl cellulose, nitrocellulose, and cellulose sulfuric esters. Examples of the starch derivatives include carboxylmethyl starch.

Examples of the synthesized polymers include polyalkyleneoxide, polyvinyl alcohol, partially acetalized polyvinyl alcohol, modified polyvinyl alcohol polyvinyl butyral, poly-N-vinyl pyrrolidone, polyethyl oxazoline, polyvinyl methyloxazoline, polyacrylic acid, polymethacrylic acid, acryloylmethylpropanesulfonic acid copolymer, polymethacrlic acid, copolymers of maleic esters or amides, polyacrylamide, polyvinylimidazole, and polyvinylpyrazole. The modified polyvinyl alcohol is described in Japanese Patent Provisional Publication No. 7(1995)-219113, and other synthesized polymers are described in European Patent No. 678770 A2.

The natural or synthesized polymers can also function as the dispersing agent described below.

As the dispersing agent, surface active agents are usable. Examples of the surface active agents include anionic surface active agents (described in U.S. Pat. Nos. 4,006,025, 5,104,776; European Patent No. 678771 A2; and Japanese Patent Provisional Publication Nos. 62(1987)-215272, 63(1988)-11935, 63(1988)-60446, 1(1989)-201655, 4(1992)-125548, and 4(1992)-324858), nonionic surface active agents, amphoteric surface active agents (described in U.S. Pat. No. 3,542,581; and European Patent No. 569074 A1), and fluorine-containing surface active agents (described in European Patent No. 602428 A1). Anionic or nonionic surface active agents are preferred. Two or more agents can be used in combination.

The natural or synthesized polymers are also usable as the dispersing agent. The polymers having low molecular weights (preferably 1,500 to 2,000) described in Japanese Patent Provisional Publication Nos. 60(1985)-158437 and 7(1995)-13300 and the nonionic polymers described in U.S. Pat. No. 3,860,425 are preferred.

The amount of the dispersing agent is preferably in the range of 1 to 200 wt. % based on that of the dye.

The fine particles of the dye preferably have a mean particle size of 0.005 to 10 μm, more preferably 0.01 to 1 μm, further preferably 0.01 to 0.5 μm, and most preferably 0.01 to 0.1 μm.

In the case that the dye (preferably, in the form of solid fine particles) is incorporated into the silver halide photographic material, the dye is contained in the silver halide emulsion layer or in the non light sensitive hydrophilic colloid layer. Which layer contains the dye depends on the purpose.

The colloid layer containing the dye functions as an antihalation layer or a filter layer. The antihalation layer is provided between the support and the emulsion layer or on the support surface opposite to the emulsion layer (i.e., on the back surface of the support). The filter layer of yellow is provided between a blue-sensitive emulsion layer and a green-sensitive one, and that of magenta is between a green-sensitive one and a red-sensitive one.

In each of the aforementioned layers (i.e., antihalation layer, yellow filter layer, and magenta filter layer), the dye of the formula (I) can be contained (preferably, in the form of solid fine particles).

The silver halide photographic material of the invention preferably comprises the arylidene or azomethine dye in an amount of $5.0 \times 10^{-5}$ to $5.0$ g/m$^2$, more preferably $5.0 \times 10^{-4}$ to $2.0$ g/m$^2$, further preferably $5.0 \times 10^{-3}$ to $1.0$ g/m$^2$. Two or more compounds of the dye can be added to a layer in combination, and a compound of the dye can be contained in two or more layers. The arylidene dye of the formula (I) can be used in combination with known dyes.

Each of the silver halide emulsion layer and the non light sensitive hydrophilic colloid layer in the photographic material is prepared from a hydrophilic colloid. A typical hydrophilic colloid is gelatin.

An emulsion of silver bromide, silver iodobromide, silver chloroiodobromide, silver chlorobromide or silver chloride is preferably used as the silver halide emulsion.

The silver halide grains may be extremely small grains having a grain diameter (diameter of projected area) of less than 0.1 μm. The grains may also be relatively large grains having a diameter of more 10 μm.

The grain size distribution is preferably monodispersed. In detail, the grains having sizes within the range of ±20% of the mean grain size are preferably not less than 60 wt. %, more preferably not less than 80 wt. % base on the total amount of the grains. The monodispersed emulsion is described in U.S. Pat. Nos. 3,574,628, 3,655,394 and British Patent No. 1,413,748.

The crystal forms of silver halide grains may be regular forms (e.g., cubic, octahedron, tetradecahedron), irregular forms (e.g., spherical form, tabular form) or mixed forms thereof. Further, the crystal may have a lattice defect (e.g., twinning plane).

The emulsion comprising tabular grains preferably contains the grains having an aspect ratio (diameter of corresponding circle per thickness) of 3 or more in an amount of not less than 50% (in terms of projected area) based on that of the total silver halide grains. The tabular grains and the preparation method thereof are described in "Photographic Science and Engineering" by Gutoff, Vol. 14(1970), pp. 248–257; U.S. Pat. Nos. 4,434,226, 4,414,310, 4,433,048, 4,439,520; and British Patent No. 2,112,157.

The silver halide emulsion can be prepared by known processes, which are described in Research Disclosure (RD), No. 17,643, pages 22 to 23 (December 1978), (Emulsion preparation and types); Research Disclosure, No. 18,716, page 648, (November 1979); Research Disclosure, No. 307,105, pages 863 to 865 (November 1989); "Chemie et Physique Photographiquen" by P. Glafkides, published by Paul Montel (1967); "Photographic Emulsion Chemistry" by G. F. Duffin, published by Focal Press (1966); and "Making and Coating Photographic Emulsion" by V. L. Zelikman et al., published by Focal Press (1964).

For preparing the emulsion containing silver halide grains having desired sizes, nucleation and grain growth are performed according to a pAg controlled double jet method. In that method, the pAg is controlled in supersaturating range under the condition that re-nucleation does not occur.

Otherwise, the emulsion can be prepared according to the method described in Japanese Patent Provisional Publication No. 54(1979)-48521. The method comprises the step of adding an aqueous solution of potassium iodide-gelatin and an aqueous solution of ammonium silver nitrate into an aqueous solution of gelatin containing silver halide grains. The adding rate varies with time. Through this method, a highly monodispersed emulsion can be obtained by optimizing the conditions such as time-dependency of the adding rate, pH, pAg, and reaction temperature. The conditions are described in "Photographic Science and Engineering" Vol. 6 (1962), pages 159 to 165; "Journal of Photographic Science" Vol. 12 (1964), pages 242 to 251; U.S. Pat. No. 3,655,394; and British Patent No. 1,413,748.

With respect to the crystal structure of the silver halide grains, the individual grains have a homogeneous halogen composition or a heterogeneous halogen composition. In the heterogeneous composition, the composition varies from the outer surface portion to the inside portion. The grains may have a multi-layered structure. The grains having the heterogeneous halogen composition are described in British Patent No. 1,027,146; U.S. Pat. Nos. 3,505,068 and 4,444, 877. Further, the silver halide grains may be conjugated with other silver halide grains having different halogen composition through epitaxial conjugation. The grains may be conjugated with compounds other than the silver halide such as silver rhodanate and lead oxide.

Preferably, the halogen composition of the grain is distributed or has a structure such as a core/shell structure or a double structure. The grains having such structures are described in Japanese Patent Publication No. 43(1968)-13162, Japanese Patent Provisional Publication Nos. 60(1985)-222845, 61(1986)-75337, and 61(1986)-215540.

Further, the grains may have a triple-structure (described in Japanese Patent Provisional Publication No. 60(1985)-222844) or a multi-layered structure. Furthermore, the grains of core/shell type having a surface covered with a thin layer of a silver halide having a different halogen composition are also usable.

The grain may have a conjugated structure as well as the enclosed structures described above. The conjugated structure is described in Japanese Patent Publication No. 58(1983)-24772; Japanese Patent Provisional Publication Nos. 58(1983)-108526, 59(1984)-16254 and 59(1984)-133540; and European Patent No. 199290 A2. In the grain having the conjugated structure, the guest (i.e., conjugating) crystal has the halogen composition different from that of the host crystal. The guest crystal connects to the edge, the corner, or the face of the host crystal, which may have a homogeneous halogen composition or a heterogeneous halogen composition such as core/shell structure.

A silver salt having a structure other than rock salt type (e.g., silver rhodanate, silver carbonate) can be combined with the silver halide to form the conjugated structure. Further, a non-silver salt such as PbO can be also conjugated with the silver halide.

In the silver iodobromide grain of core/shell type, the content of silver iodide in the core part may be either higher or lower than that in the shell part. Similarly, in the silver iodobromide grain of conjugated type, the content of silver iodide in the host crystal may be either higher or lower than that in the guest.

In the grain having a heterogeneous halogen composition, the border between halogen compositions may be clear or diffuse. The diffuse border consists of mixed crystal. Such gradual change of the halogen composition can be adopted on purpose.

The silver halide emulsion may be subjected to various treatments. For example, European Patent Nos. 0136727 B1 and 0064412 B1 disclose treatments for rounding the grains, and German Patent No. 2306447 C2 and Japanese Patent Provisional Publication No. 60(1985)-221320 disclose treatments for modifying the surface of the grains.

In the invention, the silver halide emulsion of surface latent image type is generally used. However, the emulsion of internal latent image type can be employed with an optimum developing solution or optimum developing conditions. The emulsion of internal latent image type is described in Japanese Patent Provisional Publication No. 59(1984)-133542. Further, the emulsion of superficial internal latent image type (described in Japanese Patent Provisional Publication No. 63(1988)-264740), in which the grains have thin shells, is also usable.

For promoting ripening of the silver halide emulsion, solvents for the silver halide may be used. Further, it is known that halogen ions in an excess amount promote the ripening, and hence the ripening can be also accelerated by adding a halide salt solution in place of the solvent into the reaction vessel. A ripening agent other than the solvent is also usable, and can be added into the vessel before the salts of silver and halides are added. Otherwise, the ripening agent may be poured into the vessel together with one or more silver salts, halide salts or protective colloid. Further, the agent can be introduced into the vessel independently from the addition of the salts of silver and halides.

Examples of the ripening agent other than halogen ions include ammonia, amine compounds, and thiocyanate salts such as ammonium thiocyanate and alkali metal thiocyanate (particularly, sodium thiocyanate and potassium thiocyanate).

The silver halide emulsion is usually subjected to a chemical sensitization (chalcogen sensitization, noble metal sensitization, or reduction sensitization).

In silver halide grains doped with multi-valent metal ions in an amount of more than $1 \times 10^{-4}$ mol/mol Ag, the effect caused by doping is not observed before the chemical sensitization. After the chemical sensitization, however, the effect is obtained in a remarkable degree. The sites where the chemical sensitizing nuclei are placed depend on conditions of the grains such as composition, structure and shape, and it also depends on the purpose of the emulsion. For example, the nuclei may be implanted either in the central part or in the superficial part of the grains. Further, the nuclei may be formed on the surface of the grains. If the nuclei are placed near the surface, a remarkable effect can be expected. Therefore, doping of multi-valent metal ions is more effective in the emulsion of surface latent image type than in that of internal latent image type.

The chemical sensitization can be performed with active gelatin in accordance with T. H. James, The Theory of the Photographic Process, 4th edition, pages 67 to 76 (1977). The conditions of the sensitization process may be adjusted at a pAg of 5 to 10, a pH of 5 to 8, and a temperature of 30 to 80° C. according to Research Disclosure, Vol. 120, No. 12010 (April 1974); Research Disclosure, Vol. 34, No. 13452 (June 1975); U.S. Pat. Nos. 2,642,361, 3,297,446, 3,772,031, 3,857,711, 3,901,714, 3,904,415, 4,266,018; and British Patent No. 1,315,755.

The sensitizing agents for chalcogen sensitization are compounds of sulfur, selenium, and tellurium. For noble metal sensitization, the sensitizing agents are compounds of gold, platinum, palladium, and iridium. Two or more sensitizing agents may be used in combination. In gold sensitization, a gold compound may be used in combination with thiocyanate compounds. Examples of the sulfur compounds for the sensitizing agent (i.e., sulfur sensitizing agent) include hypo, thiourea compounds, and rhodanine compounds. The sulfur sensitizing agents are described in U.S. Pat. Nos. 3,857,711, 4,266,018 and 4,054,457.

The chemical sensitization can be performed in the presence of a chemical sensitizing aid, which inhibits fogging in the sensitization process. The sensitizing aid also enhances the sensitivity. Examples of the chemical sensitizing aid include azaindene, azapyridine, and azapyrimidine. The chemical sensitizing aids (or chemical sensitization improvers) are described in U.S. Pat. Nos. 2,131,038, 3,411,914, 3,554,757; Japanese Patent Provisional Publication No. 58(1983)-126526; and G. F. Duffin, Photographic Emulsion Chemistry, pages 138 to 143.

The present invention can be effectively applied for both color photographic material and black-and-white one.

Examples of the color photographic material include color paper, color film, and color reversal film. Examples of the black-and-white photographic material include X-ray film, black-and-white film, and film for printing.

The color photographic material generally has a multilayered structure, and comprises two or more silver halide emulsion layers and two or more non light sensitive hydrophilic colloid layers. The non light sensitive hydrophilic colloid layers are a protective layer on the top emulsion layer, an intermediate layer between the emulsion layers, an undercoating layer between the bottom emulsion layer and the support, and a back layer provided on the bottom surface (on which the emulsion layer is not provided) of the support. Which layer contains the dye is determined according to the function of the dye. In the case that the dye functions as a filter, the dye is incorporated into the protective layer or the intermediate layer. On the other hand, the dye for antihalation is added into the undercoating layer or the back layer, and the dye for inhibiting irradiation is contained in the emulsion layers.

There is no particular restriction on additives of the photographic material of the invention. Examples of the additives are described in Research Disclosure, Vol. 176, No. 17643 (RD 17643) and Research Disclosure, Vol. 187, No. 18716 (RD 18716), as follows

| Additives | RD 17643 | RD 18716 |
|---|---|---|
| Chemical sensitizers | Page 23 | Page 648, right column |
| Sensitivity increasing agent | | Page 648, right column |
| Spectral sensitizing dye and Supersensitizer | Pages 23 to 24 | Page 648, right column to page 649, right column |
| Breaching agent | Page 24 | |
| Antifogging agent and stabilizer | Page 24 to 25 | Page 649, right column |
| Light absorbing agent, filter dye and ultraviolet absorbent | Pages 25 to 26 | Page 649; right column to page 650, left column |
| Stain inhibitor | Page 25 | Page 650 |
| Color image stabilizer | Page 25 | |
| Hardening agent | Page 26 | Page 651, left column |
| Binder | Page 26 | Page 651, left column |
| Plasticizer and slip agent | Page 27 | Page 650, left column |
| Coating aid and surface active agent | Pages 26 to 27 | Page 650, right column |
| Antistatic agent | Page 27 | Page 650, right column |

The dye can be incorporated into the silver halide photographic material for heat development. The material for heat development is described in U.S. Pat. No. 4,500,626; European Patent No. 210660 A2; Japanese Patent Provisional Publication Nos. 59(1984)-218443, 60(1985)-133449, and 61(1986)-238056.

The present invention is particularly suitable for development process of wet-type.

The wet development process with an automatic developing machine is described in Japanese Patent Provisional Publication Nos. 3(1991)-13937 [pages 20 to 21, 25, 30 to 33, 40, 45 to 46, 52 to 53], 3(1991)-171136 [pages 18 to 19], and 6(1994)-43583 [page 27].

The color photographic material is generally subjected after imagewise exposure to development, bleach-fix or fixing, and washing or stabilization.

The amount of the replenisher in development or fixing is preferably in the range of 25 to 200 ml, more preferably 30 to 180 ml, and further preferably 60 to 150 ml per 1 $m^2$ of the photographic material.

The processing time for development is preferably in the range of less than 5 minutes, more preferably 5 to 60 seconds, further preferably 5 to 30 seconds.

The washing process is generally performed according to counter current washing method for saving water. In place of washing, the process for stabilization can be performed according to multistage counter current stabilizing method (described in Japanese Patent Provisional Publication No. 57(1982)-8543).

The color developer is preferably an alkaline solution comprising, as a main component, a color developing agent of aromatic primary amines. Aminophenol compounds are also usable as the color developing agent, but p-phenylene diamine compounds are preferred. Examples of the p-phenylene diamine compounds include 3-methyl-4-amino- N,N-diethyl aniline, 3-methyl-4-amino-N-ethyl-N-β-hydroxyethyl aniline, 3-methyl-4-amino-N-ethyl-N-β-methanesulfoneamideethyl aniline, 3-methyl-4-amino-N-ethyl-N-β-methoxyethyl aniline, sulfates thereof, chlorides thereof, and p-toluenesulfonates thereof.

In the case that the reversal process is performed, the color development is usually carried out after black-and-white development. Examples of the black-and-white development agent include dihydroxybenzenes (e.g., hydroquinone), 3-pyrazolidones (e.g., 1-phenyl-3-pyrazolidone), and aminophenols (e.g., N-methyl-p-aminophenol).

The color or black-and-white developer generally has a pH of 9 to 12.

The emulsion layer is usually bleached after development. The bleach process may be carried out together with fixing (i.e., bleach-fix process) or independently from the fixing process. Further, for rapid processing, the bleach-fix may be performed after the bleach process. For either bleaching bath or bleach-fix bath, iron (III) aminopolycarbonate complex salts are advantageously used. The pH of the bleaching or bleach-fix bath containing the above salt is usually in the range of 5.5 to 8, but it may be lower than this range for rapid processing.

A bleaching promoter can be used, if needed, for bleaching bath, bleach-fix bath, or prebath thereof. Examples of the bleaching promoter are compounds having mercapto or disulfido group. The bleaching promoter may be incorporated in the photographic material.

As a fixing agent, thiosulfates are generally used.

After desilvering, the photographic material is generally subjected to washing or stabilizing process. The amount of water for washing is determined according to various conditions (characteristics and use of the material, temperature of water, number of washing tanks, and replenishing system such as down-flow system or counter current system). The relation between the number of washing tanks and the amount of water in the multistage counter current washing system is described in Journal of the Society of Motion Picture and Television Engineers, Vol. 64, pages 248 to 253 (May 1955).

EXAMPLE 1

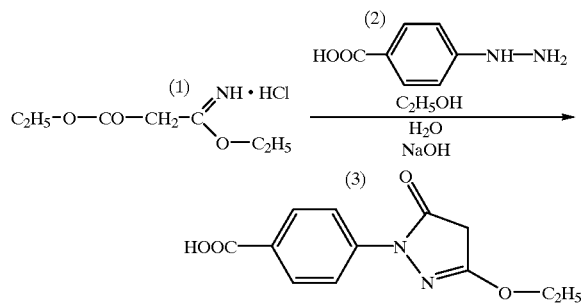

Synthesis of Compound (3)

In a three neck distillation flask, 1.2 liter of ethanol and 308 g of the compound (1) were placed. To the flask, 228 g of the compound (2) was added for 10 minutes at room temperature with stirring. After the mixture was further stirred for 3 hours, a solution prepared by dissolving 198 g of sodium hydroxide in 1,080 ml of water was then dropwise added for 1 hour. When the addition was finished, the temperature in the flask was 35° C. After further stirring for 1.5 hours, the reaction mixture was poured into 6 L of methanol. 412 ml of concentrated hydrochloric acid was dropwise added for 30 minutes, and the mixture was stirred for 1 hour. The mixture was then filtered under a reduced pressure to collect the deposited crystalline precipitate. The precipitate was washed with water and dried to obtain 354 g of the compound (3) [Yield: 95%].

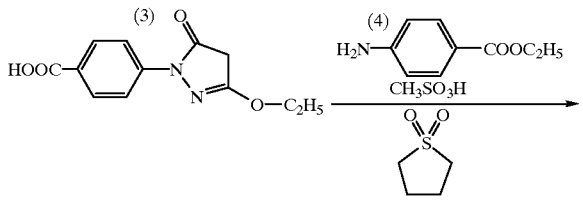

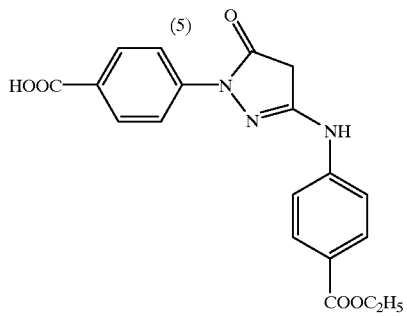

Synthesis of Compound (5)

In a three neck distillation flask, 400 ml of sulfolane was placed. To the flask, 310 g of the compound (3) was added with stirring under nitrogen gas atmosphere, and successively 268 g of the compound (4) was added. The mixture was heated to 90° C., and 24.0 g of methanesulfonic acid was dropwise added for 3 minutes at that temperature. After heating and stirring for 1 hour at 135° C., the mixture was cooled and poured into 1.5 liter of methanol with stirring. The mixture was further stirred for 1 hour, and filtered under a reduced pressure to collect the deposited crystalline precipitate. The precipitate was dried to obtain 404 g of the compound (5) [Yield: 88%].

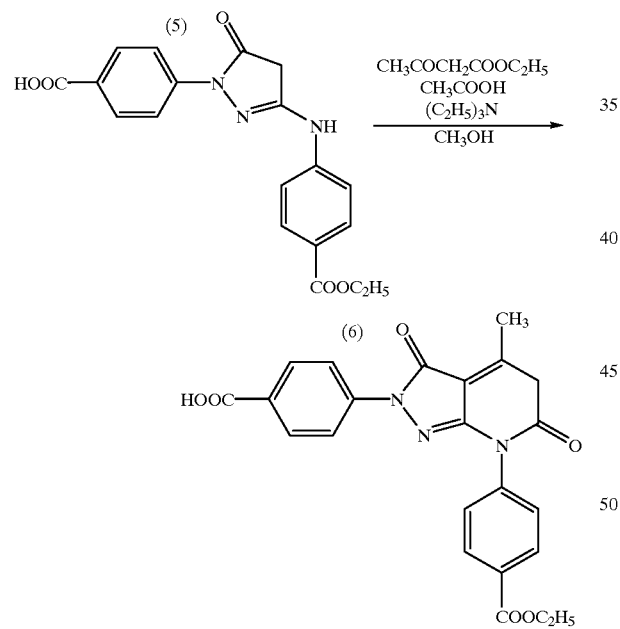

Synthesis of Compound (6)

In a three neck distillation flask, 420 g of acetic acid was placed. While the flask was cooled with ice bath so that the temperature in the flask might not be more than 50° C., 283 g of triethylamine was dropwise added. Further, 257 g of the compound (5) and 109.3 g of ethyl acetoacetate were successively added. After heating and stirring for 5 hours at 90° C., the mixture was cooled and poured into 2 liters of methanol with stirring. To the mixture, 292 ml of concentrated hydrochloric acid was dropwise added for 30 minutes. The mixture was stirred for 1 hour, and filtered under a reduced pressure to collect the deposited crystalline precipitate. The precipitate was dried to obtain 280 g of the compound (6) [Yield: 92%].

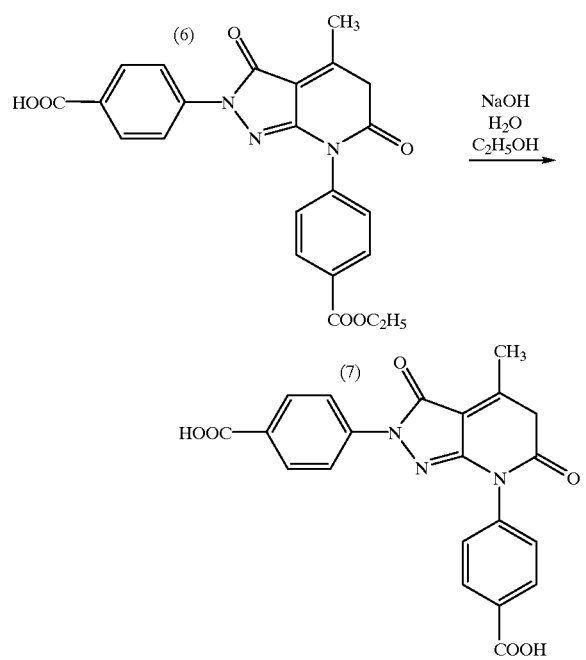

Synthesis of Compound (7)

In a three neck distillation flask, 260 g of the compound (6) and 1.2 liter of ethanol were placed. To the flask, a solution prepared by dissolving 120 g of sodium hydroxide in 650 ml of water was dropwise added for 30 minutes with stirring. The mixture was further stirred for 2 hours, and then poured into 2.2 liters of methanol. To the mixture, 330 ml of concentrated hydrochloric acid was dropwise added for 20 minutes with stirring. The mixture was further stirred for 1 hour, and filtered under a reduced pressure to collect the deposited crystalline precipitate. The precipitate was dried to obtain 241 g of the compound (7) [Yield: 99%].

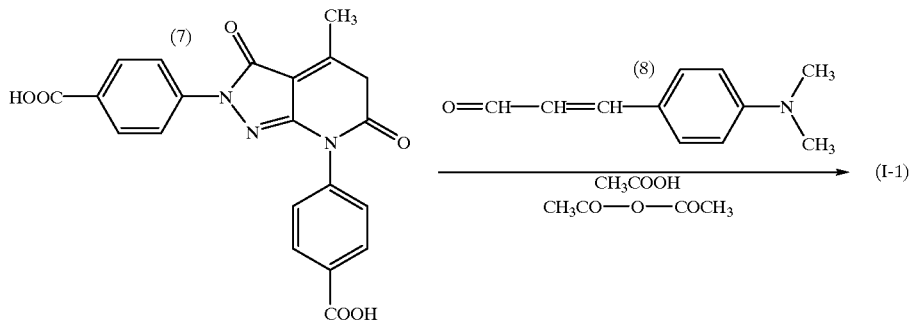

Synthesis of Arylidene Compound (I-1)

In a three neck distillation flask, 109.4 g of the compound (7), 56.8 g of the compound (8) and 2.2 liters of acetic acid were placed. To the flask, 193 g of acetic anhydride was added with stirring. After heating and stirring for 2 hours at 100° C., the mixture was cooled to room temperature. The mixture was filtered under a reduced pressure to collect the deposited crystalline precipitate. The precipitate was successively washed with acetic acid, acetone, and methanol in this order to obtain 384 g of the arylidene compound (I-1) in the form of methanol wet cake [Yield: 97%, Content of the dye: 38.3%].

EXAMPLE 2

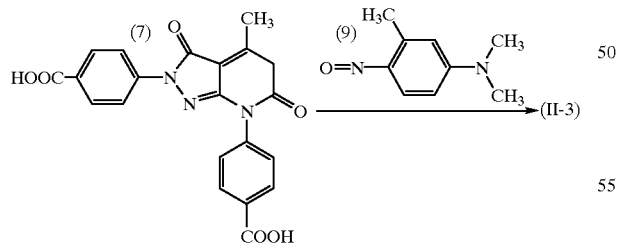

Synthesis of Azomethine Compound (II-3)

In a three neck distillation flask, 203 g of the compound (7) prepared in Example 1 and 600 ml of methanol were placed. To the flask, 70 ml of triethylamine was added with stirring at room temperature. The mixture was further stirred for 10 minutes, and 100 g of the compound (9) was added. Successively, 52 ml of acetic anhydride was dropwise added for 30 minutes. The mixture was stirred for 4 hours at room temperature, and then filtered under a reduced pressure to collect the deposited crystalline precipitate. The precipitate was successively washed with methanol, acetone, and methanol in this order to obtain 488 g of the azomethine compound (II-3) in the form of methanol wet cake [Yield: 85%, Content of the dye: 48.3%].

EXAMPLE 3

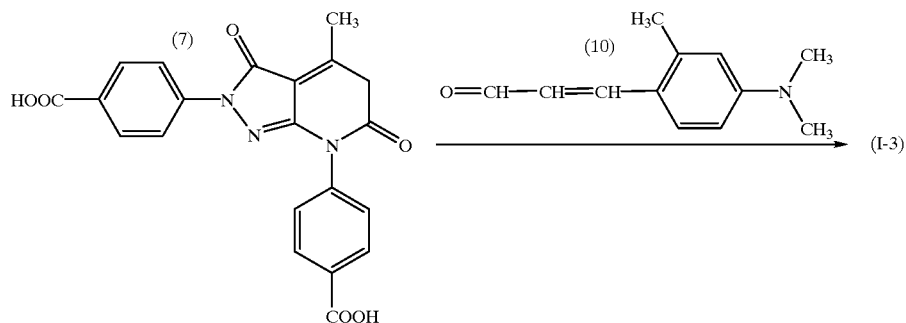

Synthesis of Arylidene Compound (I-3)

In a three neck distillation flask, 109.4 g of the compound (7) prepared in Example 1, 61.3 g of the compound (10) and 2.5 liters of acetic acid were placed. To the flask, 193 g of acetic anhydride was added with stirring. The mixture was heated and refluxed for 4 hours with stirring, and then cooled to room temperature. The resulting mixture was filtered under a reduced pressure to collect the deposited crystalline precipitate. The precipitate was successively washed with acetic acid, methanol, acetone, and methanol in this order to obtain 350 g of the arylidene compound (I-3) in the form of methanol wet cake [Yield: 97%, Content of the dye: 43.0%].

EXAMPLE 4

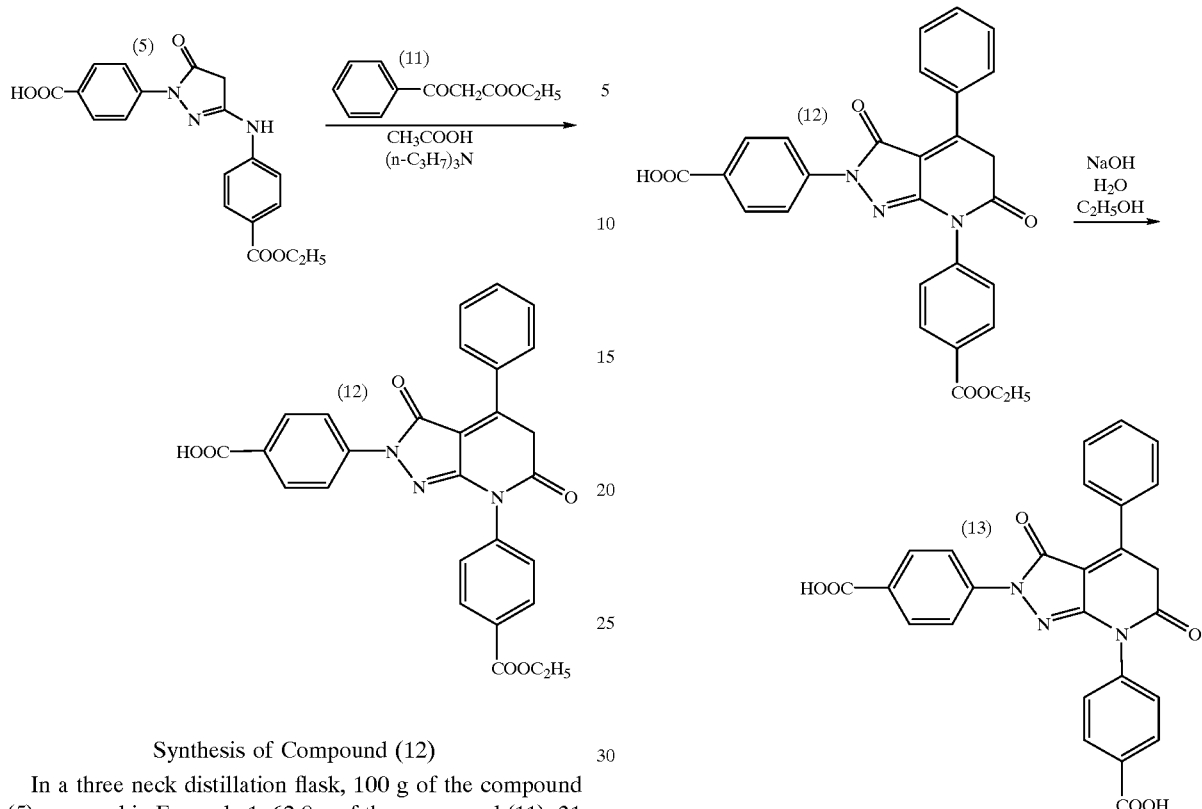

Synthesis of Compound (12)

In a three neck distillation flask, 100 g of the compound (5) prepared in Example 1, 62.8 g of the compound (11), 31 ml of acetic acid and 200 ml of ethylene glycol were placed. To the flask, 310 ml of tri-n-propylamine was dropwise added at room temperature. After heating and stirring for 3 hours at 110° C., the mixture was cooled to 40° C. and poured into 1,000 g of ice. To the mixture, 280 ml of concentrated hydrochloric acid was dropwise added for 10 minutes with stirring. The mixture was further stirred for 1 hour, and filtered under a reduced pressure to collect the deposited crystalline precipitate. The precipitate and 300 ml of acetonitrile were mixed, and refluxed for 1 hour with stirring. The mixture was cooled to room temperature, and filtered under a reduced pressure to collect the deposited crystalline product. Thus, 115.3 g of the compound (12) was obtained [Yield: 85%].

Synthesis of Compound (13)

In a three neck distillation flask, 49.5 g of the compound (12) and 250 ml of methanol were placed. To the flask, a solution prepared by dissolving 20 g of sodium hydroxide in 40 ml of water was added for 5 minutes with stirring at room temperature. After further stirring for 2 hours, the mixture was poured into 400 g of ice. To the mixture, 86 ml of concentrated hydrochloric acid was added with stirring. The mixture was further stirred for 10 minutes, and concentrated by means of a rotary evaporator to obtain a residue of the compound (13). The product was not further purified and used in the following synthesis.

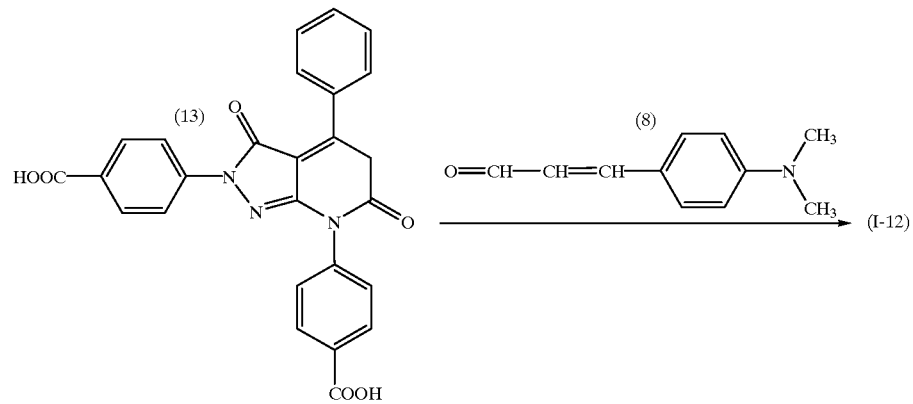

Synthesis of Arylidene Compound (I-12)

The above product of the compound (13), 21.0 g of the compound (8), 150 ml of acetic acid, and 66.0 ml of acetic anhydride were placed in a three neck distillation flask. The mixture was heated and stirred for 4 hours at 90° C., and cooled to 50° C. After adding 150 ml of methanol, the mixture was cooled to room temperature and filtered under a reduced pressure to collect the deposited crystalline precipitate. The precipitate was successively washed with methanol, acetone, water, and methanol in this order to obtain 130.1 g of the arylidene compound (I-12) in the form of methanol wet cake [Yield: 95% based on the amount of the compound (12), Content of the dye: 45.6%].

EXAMPLE 5

Dispersion of Solid Fine Particles of Dye

In a 700 ml pot mill, 21.7 ml of water, 3 ml of 5 wt. % aqueous solution of sodium p-octylphenoxyethoxyethanesulfonate and 0.5 g of 5 wt. % aqueous solution of p-octylphenoxypolyoxyethylene ether (polymerization degree: 10) were placed. To the pot, 5.0 g of the arylidene compound (I-1) and 500 ml of zirconium oxide beads (diameter: 1 mm) were added, and mixed for 2 hours by using an oscillating ball mill (BO type, Chuo-Koki Co., Ltd.). The obtained mixture was collected, and 8 g of 2.5 wt. % aqueous solution of gelatin was added to the mixture. The resulting mixture was filtered to remove the beads. Thus, a gelatin dispersion of the arylidene compound (I-1) was prepared [mean particle size of dye: 0.36 μm].

Preparation of Silver Halide Photoaraphic Material

A color silver halide photographic material having the following layered structure (described in Japanese Patent Provisional Publication No. 11(1999)-38568) was prepared. The 2nd layer (second antihalation layer) contains the dispersion of solid fine particles of the arylidene compound (I-1) in an amount of 0.10 g/m².

16th layer (second protective layer)
15th layer (first protective layer)
14th layer (blue high sensitive emulsion layer)
13th layer (blue low sensitive emulsion layer)
12th layer (yellow filter layer)
11th layer (green high sensitive emulsion layer)
10th layer (green middle sensitive emulsion layer)
9th layer (green low sensitive emulsion layer)
8th layer (inter-image effect layer)
7th layer (intermediate layer)
6th layer (red high sensitive emulsion layer)
5th layer (red middle sensitive emulsion layer)
4th layer (red low sensitive emulsion layer)
3rd layer (intermediate layer)
2nd layer (second antihalation layer)
1st layer (first antihalation layer)
Undercoating layer
Support (cellulose triacetate film)

The compositions of the 2nd layer (second antihalation layer) were as follows. The layers other than the 2nd layer comprise the same compositions as those of generally known color silver halide photographic materials.

| Compositions of the 2nd layer | |
|---|---|
| Black colloidal silver | 0.066 g/m² |
| Gelatin | 0.407 g/m² |
| The following magenta coupler | 0.050 g/m² |
| The following cyanine dye | 0.002 g/m² |
| Tricresyl phosphate (solvent of high boiling point) | 0.074 g/m² |
| The solid fine particles of arylidene dye (I-1) | 0.015 g/m² |

Magenta coupler

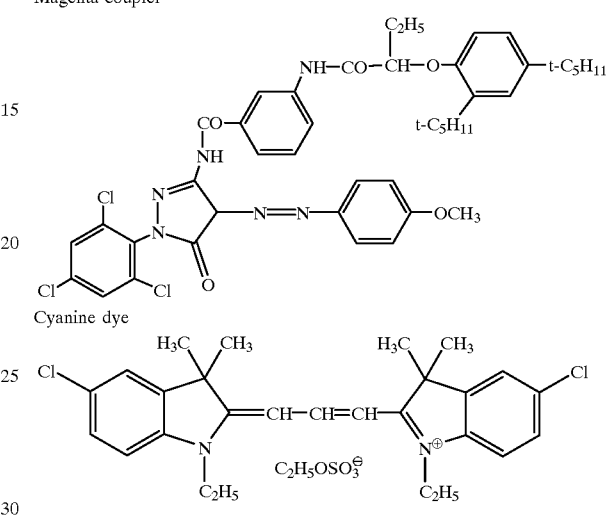

Cyanine dye

Evaluation of Photographic Material

The photographic material was exposed to white light through an optical wedge, and then processed by means of an automatic developing machine in the following manner. The machine was beforehand adjusted, and the process was performed until the amount of replenisher accumulated to the volume of three times as large as that of the mother liquid tanks.

| Process | Time | Temperature |
|---|---|---|
| Color development | 3 minutes and 15 seconds | 38° C. |
| Bleaching | 3 minutes and 0 second | 38° C. |
| Washing | 0 minute and 30 seconds | 24° C. |
| Fixing | 3 minutes and 0 second | 38° C. |
| Washing (1) | 0 minute and 30 seconds | 24° C. |
| Washing (2) | 0 minute and 30 seconds | 24° C. |
| Stabilizing | 0 minute and 30 seconds | 38° C. |
| Drying | 4 minutes and 20 seconds | 55° C. |

Color developing solution

| | |
|---|---|
| Diethylenetriamine pentaacetic acid | 1.0 g |
| 1-Hydroxyethylidene-1,1-diphosphonic acid | 2.0 g |
| Sodium sulfite | 4.0 g |
| Potassium carbonate | 30.0 g |
| Potassium bromide | 1.4 g |
| Potassium iodide | 1.5 mg |
| Sulfate salt of hydroxyl amine | 2.4 g |
| 4-(N-ethyl-N-β-hydroxyethylamino)2-methylaniline sulfate | 4.5 g |
| Water (make up to) | 1 liter |
| pH (adjusted with potassium hydroxide and sulfuric acid) | 10.05 |

Bleach-fix bath

| | |
|---|---|
| Sodium iron(III) ethylenediaminetetraacetate trihydrate | 100.0 g |
| Disodium ethylenediaminetetraacetate | 10.0 g |
| 3-mercapto-1,2,4-triazole | 0.03 g |

| | |
|---|---|
| -continued | |
| Ammonium bromide | 140.0 g |
| Ammonium nitrate | 30.0 g |
| Aqueous ammonia (27%) | 6.5 ml |
| Water (make up to) | 1 liter |
| pH (adjusted with aqueous ammonia and nitric acid) | 6.0 |
| Fixing solution | |
| Disodium ethylenediaminetetraacetate | 0.5 g |
| Ammonium sulfite | 20.0 g |
| Aqueous solution (70%) of ammonium thiosulfate | 295.0 ml |
| Acetic acid (90%) | 3.3 g |
| Water (make up to) | 1 liter |
| pH (adjusted with aqueous ammonia and acetic acid) | 6.7 |
| Stabilizing solution | |
| p-Nonylphenoxypolyglycidol (mean polymerization degree: 10) | 0.2 g |
| Ethylenediaminetetraacetic acid | 0.05 g |
| 1,2,4-Triazole | 1.3 g |
| 1,4-Bis(1,2,4-triazole-1-ylmethyl)piperazine | 0.75 g |
| Hydroxyacetic acid | 0.02 g |
| Hydroxyethyl cellulose | 0.1 g |
| 1,2-Benzisothiazoline-3-one | 0.05 g |
| Water (make up to) | 1 liter |
| pH | 8.5 |

The photographic density of the processed material was measured to determine the density [DR(min)] in the fogged area of the red-sensitive emulsion layers. The obtained DR(min) was evaluated in terms of a relative value based on the result of Comparison Example 1 described below. From the obtained DR(min) value, the decoloring of the dye was estimated. Generally, a small value of DR(min) in the fogged area means that the dye is decolored well.

Further, the sensitivity of the red-sensitive emulsion layers was evaluated in terms of a relative value. The value of the relative sensitivity was determined by measuring the amount of light to cause the fog density of +0.2, calculating the logarithmic reciprocal of the measured amount, and converting the calculated value into a relative value based on the result of Comparison Example 1 described below. Generally, a high relative sensitivity means that the dye in the second antihalation layer hardly diffuses into the red-sensitive emulsion layer.

The stability of the dye was also estimated in the following manner. First, the reflection spectrum (in the wavelength region of 400 to 700 nm) of the photographic material before exposure was measured under an IR lamp. The material was then stored in a black box for 10 days at the temperature of 50° C. and the relative humidity of 80%. After that, the reflection spectrum in the above wavelength region was again measured under the IR lamp. The ratios of the absorbance at 550 nm and 650 nm were calculated according to the following formula, to estimate the stability of the dye.

Stability of dye (absorbance ratio)=100×(absorbance before storing)/(absorbance after storing)

The results are set forth in Table 1.

EXAMPLES 6–12

The procedure of Example 5 was repeated except for using 5.0 g of arylidene compound (I-3), (I-6), (I-12), (I-14), (I-16), or azomethine compound (II-3) or (II-9) in place of 5.0 g of arylidene compound (I-1), to prepare a dispersion of solid fine particles of the dye. The mean particle size of each dispersion was set forth in Table 1.

The procedure of Example 5 was repeated except for using each prepared dispersion to prepare the silver halide photosensitive material. The prepared material was evaluated in the same manner as Example 5.

The results are set forth in Table 1.

COMPARISON EXAMPLES 1–6

The procedure of Example 5 was repeated except for using 5.0 g of oxonol compound (X-1), (X-2), azomethine compound (Y-1), (Y-2), or arylidene compound (Z-1) or (Z-2) shown below in place of 5.0 g of arylidene compound (I-1), to prepare a dispersion of solid fine particles of the dye. The mean particle size of each dispersion was set forth in Table 1.

The azomethine compounds (Y-1), (Y-2), and the arylidene compounds (Z-1) and (Z-2) are described in Japanese Patent Provisional Publication No. 3(1991)-7931 as the compounds (5), (7), (27), and (6), respectively.

The procedure of Example 5 was repeated except for using each prepared dispersion to prepare the silver halide photosensitive material. The prepared material was evaluated in the same manner as Example 5.

The results are set forth in Table 1.

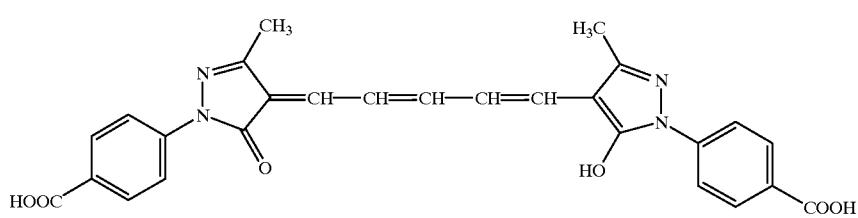

(X-1)

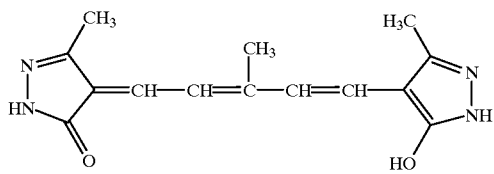

(X-2)

-continued
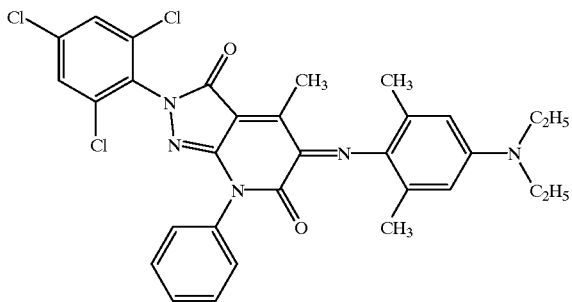
(Y-1)
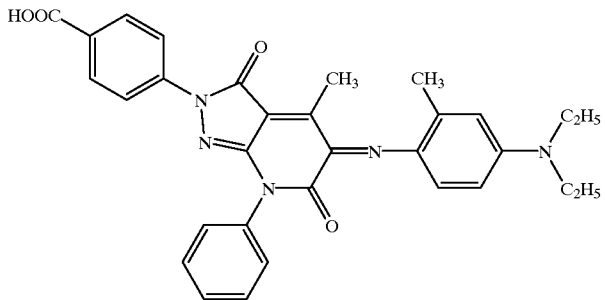
(Y-2)
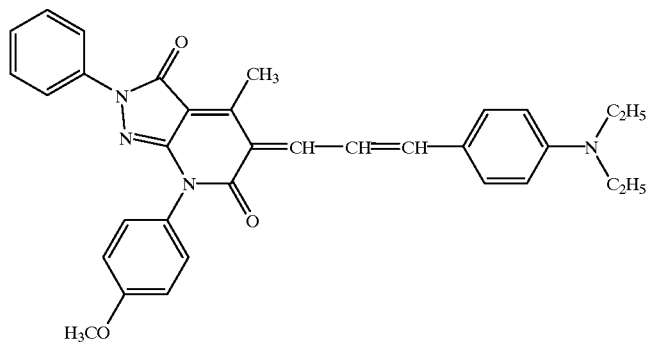
(Z-1)
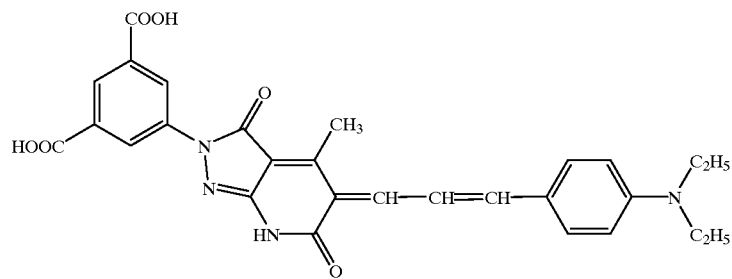
(Z-2)
TABLE 1
|  | Dye | Mean particle size of dye | Emulsion layer* D(min) | Emulsion layer* sen** | Stability 550 nm | Stability 650 nm |
|---|---|---|---|---|---|---|
| Ex. 5 | I-1 | 0.36 μm | −0.10 | +0.07 | 92 | 96 |
| Ex. 6 | I-3 | 0.42 μm | −0.04 | +0.06 | 90 | 92 |
| Ex. 7 | I-6 | 0.30 μm | −0.02 | +0.05 | 92 | 95 |
| Ex. 8 | I-12 | 0.50 μm | −0.05 | +0.07 | 94 | 96 |
| Ex. 9 | I-14 | 0.33 μm | −0.08 | +0.06 | 88 | 86 |
| Ex. 10 | I-16 | 0.41 μm | −0.12 | +0.06 | 84 | 82 |
| Ex. 11 | II-3 | 0.33 μm | −0.08 | +0.05 | 91 | 95 |
TABLE 1-continued
|  | Dye | Mean particle size of dye | Emulsion layer* D(min) | Emulsion layer* sen** | Stability 550 nm | Stability 650 nm |
|---|---|---|---|---|---|---|
| Ex. 12 | II-9 | 0.36 μm | −0.07 | +0.05 | 90 | 92 |
| C. Ex. 1 | X-1 | 0.44 μm | 0*** | 0*** | 76 | 65 |
| C. Ex. 2 | X-2 | 0.24 μm | +0.24 | −0.04 | 59 | 44 |
| C. Ex. 3 | Y-1 | 0.40 μm | +0.44 | −0.07 | 80 | 83 |
| C. Ex. 4 | Y-2 | 0.32 μm | +0.27 | −0.09 | 84 | 84 |

TABLE 1-continued

| | | Emulsion layer* | | Stability | |
|---|---|---|---|---|---|
| Dye | Mean particle size of dye | D(min) | sen** | 550 nm | 650 nm |
| C. Ex. 5 Z-1 | 0.48 μm | +0.33 | −0.13 | 78 | 70 |
| C. Ex. 6 Z-2 | 0.31 μm | +0.14 | −0.12 | 77 | 60 |

Remarks)
*: red-sensitive silver halide emulsion layer,
**: relative sensitivity,
***: standards for D(min) and relative sensitivity.

EXAMPLE 13

Preparation of Silver Halide Photographic Material

An X-ray photographic material having the following layered structure (described in Japanese Patent Provisional Publication No. 3(1991)-7931, Example 5) was prepared. The dye layers contain the dispersion of solid fine particles of arylidene compound (I-1) prepared in Example 1.

Surface protective layer
X-ray sensitive silver halide emulsion layer
Dye layer (comprising gelatin and the dye dispersion in amounts of 0.12 g/m² and 50 mg/m², respectively)
Support (polyethylene terephthalate film colored in blue and having the thickness of 175 μm)
Dye layer (comprising gelatin and the dye dispersion in amounts of 0.12 g/m² and 50 mg/M², respectively)
X-ray sensitive silver halide emulsion layer
Surface protective layer Evaluation of Photoaraphic Material The photographic material was placed between two screens (G-3, Fuji Photo Film Co., Ltd.), and exposed to X-rays through a water phantom of 10 cm.

The exposed material was processed by means of an automatic developing machine (FPM-4000, Fuji Photo Film Co., Ltd.).

The sensitivity was determined in terms of a relative value providing that the sensitivity of a sample without dye was set at 100.

The sharpness (MTF) was also evaluated at the area having the optical density of 1.0 [aperture: 30 μm×500 μm. spatial frequency: 1.0 cycle/mm].

Further, the unexposed material was processed by means of the machine to estimate decoloring. The degree of decoloring was evaluated as 5 grades A to E. The grade A means that the dye was completely decolored, and the grade E means that the color remained in a considerable degree. The grades B to D indicate intermediate degrees between the grades A and E.

The results are set forth in Table 2.

EXAMPLES 14–20

The procedure of Example 1 was repeated except for using 5.0 g of arylidene compound (I-4), (I-18), (I-25), or azomethine compound (II-1), (II-6) or (II-11) in place of 5.0 g of arylidene compound (I-1), to prepare a dispersion of solid fine particles of the dye. The mean particle size of each dispersion was set forth in Table 2.

The procedure of Example 13 was repeated except for using each prepared dispersion and arylidene compound (I-12) prepared in Example 8, to prepare the silver halide photosensitive material. The prepared material was evaluated in the same manner as Example 13.

The results are set forth in Table 2.

COMPARISON EXAMPLE 7

The procedure of Example 13 was repeated except for using the dispersion of solid fine particles of azomethine compound (Y-2) prepared in Comparison Example 4, to prepare the silver halide photosensitive material. The prepared material was evaluated in the same manner as Example 5.

The results are set forth in Table 2.

TABLE 2

| | Dye | Mean particle size of dye | Relative sensitivity | MTF | Decoloring degree |
|---|---|---|---|---|---|
| Ex. 13 | I-1 | 0.36 μm | 95 | 0.89 | A |
| Ex. 14 | I-4 | 0.42 μm | 94 | 0.88 | A |
| Ex. 15 | I-12 | 0.50 μm | 94 | 0.88 | A |
| Ex. 16 | I-18 | 0.44 μm | 96 | 0.88 | A |
| Ex. 17 | I-25 | 0.32 μm | 94 | 0.88 | A |
| Ex. 18 | II-1 | 0.49 μm | 94 | 0.88 | A |
| Ex. 19 | II-6 | 0.28 μm | 95 | 0.89 | A |
| Ex. 20 | II-11 | 0.50 μm | 93 | 0.88 | A |
| C. Ex. 7 | Y-2 | 0.41 μm | 90 | 0.81 | B |

EXAMPLE 21

Preparation of Silver Halide Photoaraphic Material

A photographic material having the following layered structure (described in Japanese Patent Provisional Publication No. 3(1991)-7931, Example 7) was prepared. The antihalation layer contains the dispersion of solid fine particles of arylidene compound (I-1) in the amount of 0.10 g/m².

7th layer (protective layer)
6th layer (UV absorbing layer)
5th layer (IR-sensitive cyan-color emulsion layer)
4th layer (UV absorbing layer)
3rd layer (IR-sensitive magenta-color emulsion layer)
2nd layer (layer for preventing colors from mixing)
1st layer (IR-sensitive yellow-color emulsion layer)
Antihalation layer (comprising gelatin and the dye dispersion in amounts of 0.8 g and 77 mg, respectively)
Support (paper having both faces laminated with polyethylene films)

Evaluation of Photoaraphic Material

The photographic material was imagewise exposed, and processed by means of a color paper processor. Thus obtained image exhibited high resolution and sharp edge.

EXAMPLES 22–27

The procedure of Example 1 was repeated except for using 5.0 g of arylidene compound (I-8), (I-19), or azomethine compound (II-4), (II-7) or (II-8) in place of 5.0 g of arylidene compound (I-1), to prepare a dispersion of solid fine particles of the dye.

The procedure of Example 21 was repeated except for using each prepared dispersion and arylidene compound (I-12) prepared in Example 8, to prepare the silver halide photosensitive material. The prepared material was evaluated in the same manner as Example 21, and it was confirmed that each material gave an image exhibiting high resolution and sharp edge.

We claim:

1. An arylidene compound represented by the formula (I):

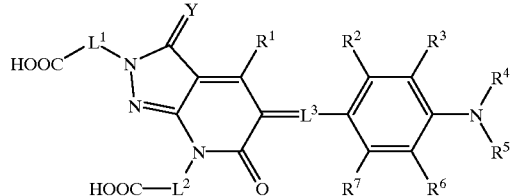

(I)

wherein each of $L^1$ and $L^2$ independently is a divalent aliphatic group, a divalent aromatic group or a divalent heterocyclic group; $L^3$ is trimethine, pentamethine or heptamethine; Y is =O, =S or =N—$R^{10}$, in which $R^{10}$ is hydrogen, an aliphatic group, an aromatic group or a heterocyclic group; $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —N$R^{15}R^{16}$, —CO—N$R^{17}R^{18}$, —$SO_2$—$R^{19}$ or —$SO_2$—N$R^{20}R^{21}$, in which each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group; each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —N$R^{25}R^{26}$, —NHCO—$R^{27}$, —NH—CO—O—$R^{28}$, —$SO_2$—$R^{29}$ or —NH—$SO_2$—$R^{30}$, in which each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group; each of $R^4$ and $R^5$ independently is hydrogen, an aliphatic group, an aromatic group, —CO—$R^{31}$ or —$SO_2$—$R^{32}$, in which each of $R^{31}$ and $R^{32}$ independently is an aliphatic group or an aromatic group; and $R^2$ and $R^3$, $R^3$ and $R^4$, $R^4$ and $R^5$, $R^5$ and $R^6$ or $R^6$ and $R^7$ can be combined with each other to form a ring.

2. The arylidene compound as claimed in claim 1, wherein $L^3$ is trimethine.

3. The arylidene compound as claimed in claim 1, wherein Y is =O.

4. The arylidene compound as claimed in claim 1, wherein $R^1$ is hydrogen, an aliphatic group or an aromatic group.

5. The arylidene compound as claimed in claim 1, wherein each of $R^2$ and $R^7$ independently is hydrogen, an alkyl group or an alkoxy group; each of $R^3$ and $R^6$ is hydrogen; each of $R^4$ and $R^5$ independently is hydrogen, an alkyl group, or an aryl group; and $R^3$ and $R^4$ or $R^5$ and $R^6$ can be combined with each other to form a ring.

6. A silver halide photographic material comprising a support, a silver halide emulsion layer and a non-light-sensitive hydrophilic colloidal layer, wherein the silver halide emulsion layer or the non-light-sensitive hydrophilic colloidal layer contains an arylidene dye represented by the formula (I):

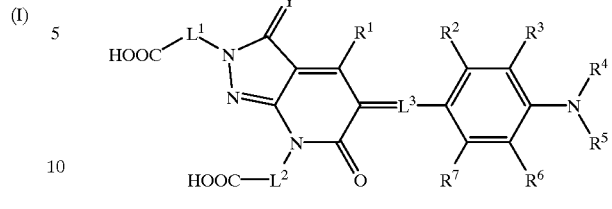

(I)

wherein each of $L^1$ and $L^2$ independently is a divalent aliphatic group, a divalent aromatic group or a divalent heterocyclic group; $L^3$ is trimethine, pentamethine or heptamethine; Y is =O, =S or =N—$R^{10}$, in which $R^{10}$ is hydrogen, an aliphatic group, an aromatic group or a heterocyclic group; $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —N$R^{15}R^{16}$, —CO—N$R^{17}R^{18}$, —$SO_2$—$R^{19}$ or —$SO_2$—N$R^{20}R^{21}$, in which each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group; each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —N$R^{25}R^{26}$, —NHCO—$R^{27}$, —NH—CO—O—$R^{28}$, —$SO_2$—$R^{29}$ or —NH—$SO_2$—$R^{30}$, in which each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group; each of $R^4$ and $R^5$ independently is hydrogen, an aliphatic group, an aromatic group, —CO—$R^{31}$ or —$SO_2$—$R^{32}$, in which each of $R^{31}$ and $R^{32}$ independently is an aliphatic group or an aromatic group; and $R^2$ and $R^3$, $R^3$ and $R^4$, $R^4$ and $R^5$, $R^5$ and $R^6$ or $R^6$ and $R^7$ can be combined with each other to form a ring.

7. The silver halide photographic material as claimed in claim 6, wherein the arylidene dye represented by the formula (I) is in the form of solid fine particles which are dispersed in the silver halide emulsion layer or in the non-light-sensitive hydrophilic colloidal layer.

8. The silver halide photographic material as claimed in claim 6, wherein $L^3$ is trimethine.

9. The silver halide photographic material as claimed in claim 6, wherein Y is =O.

10. The silver halide photographic material as claimed in claim 6, wherein $R^1$ is hydrogen, an aliphatic group or an aromatic group.

11. The silver halide photographic material as claimed in claim 6, wherein each of $R^2$ and $R^7$ independently is hydrogen, an alkyl group or an alkoxy group; each of $R^3$ and $R^6$ is hydrogen; each of $R^4$ and $R^5$ independently is hydrogen, an alkyl group, or an aryl group; and $R^3$ and $R^4$ or $R^5$ and $R^6$ can be combined with each other to form a ring.

12. An azomethine compound represented by the formula (II):

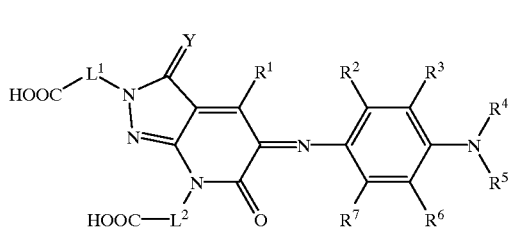
(II)

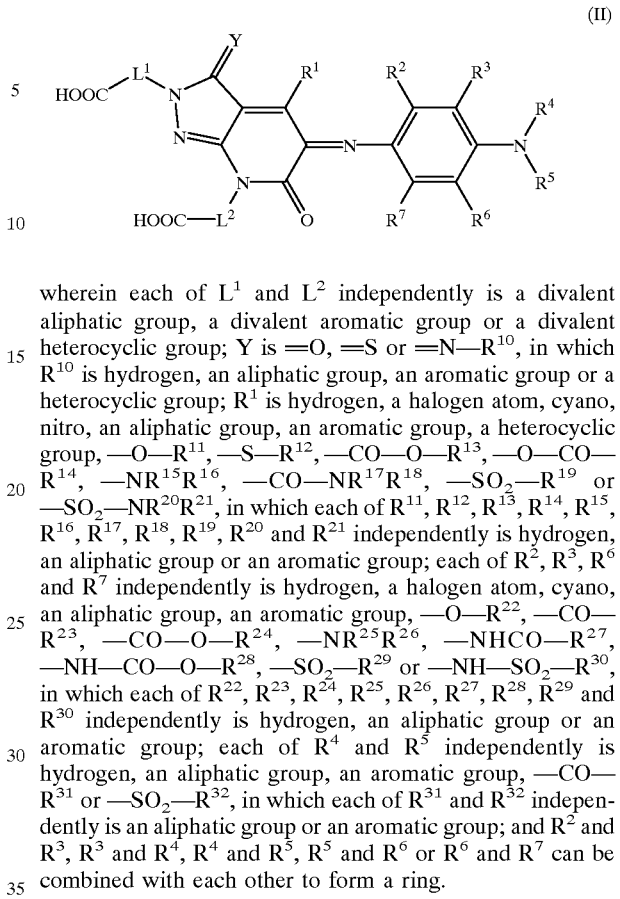
(II)

wherein each of $L^1$ and $L^2$ independently is a divalent aliphatic group, a divalent aromatic group or a divalent heterocyclic group; Y is =O, =S or =N—$R^{10}$, in which $R^{10}$ is hydrogen, an aliphatic group, an aromatic group or a heterocyclic group; $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —N$R^{15}R^{16}$, —CO—N$R^{17}R^{18}$, —SO$_2$—$R^{19}$ or —SO$_2$—N$R^{20}R^{21}$, in which each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group; each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —N$R^{25}R^{26}$, —NHCO—$R^{27}$, —NH—CO—O—$R^{28}$, —SO$_2$—$R^{29}$ or —NH—SO$_2$—$R^{30}$, in which each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group; each of $R^4$ and $R^5$ independently is hydrogen, an aliphatic group, an aromatic group, —CO—$R^{31}$ or —SO$_2$—$R^{32}$, in which each of $R^{31}$ and $R^{32}$ independently is an aliphatic group or an aromatic group; and $R^2$ and $R^3$, $R^3$ and $R^4$, $R^4$ and $R^5$, $R^5$ and $R^6$ or $R^6$ and $R^7$ can be combined with each other to form a ring.

13. The azomethine compound as claimed in claim 12, wherein Y is =O.

14. The azomethine compound as claimed in claim 12, wherein $R^1$ is hydrogen, an aliphatic group, or an aromatic group.

15. The azomethine compound as claimed in claim 12, wherein each of $R^2$ and $R^7$ independently is hydrogen, an alkyl group or an alkoxy group; each of $R^3$ and $R^6$ is hydrogen; each of $R^4$ and $R^5$ independently is hydrogen, an alkyl group, or an aryl group; and $R^3$ and $R^4$ or $R^5$ and $R^6$ can be combined with each other to form a ring.

16. A silver halide photographic material comprising a support, a silver halide emulsion layer and a non-light-sensitive hydrophilic colloidal layer, wherein the silver halide emulsion layer or the non-light-sensitive hydrophilic colloidal layer contains an azomethine dye represented by the formula (II):

wherein each of $L^1$ and $L^2$ independently is a divalent aliphatic group, a divalent aromatic group or a divalent heterocyclic group; Y is =O, =S or =N—$R^{10}$, in which $R^{10}$ is hydrogen, an aliphatic group, an aromatic group or a heterocyclic group; $R^1$ is hydrogen, a halogen atom, cyano, nitro, an aliphatic group, an aromatic group, a heterocyclic group, —O—$R^{11}$, —S—$R^{12}$, —CO—O—$R^{13}$, —O—CO—$R^{14}$, —N$R^{15}R^{16}$, —CO—N$R^{17}R^{18}$, —SO$_2$—$R^{19}$ or —SO$_2$—N$R^{20}R^{21}$, in which each of $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently is hydrogen, an aliphatic group or an aromatic group; each of $R^2$, $R^3$, $R^6$ and $R^7$ independently is hydrogen, a halogen atom, cyano, an aliphatic group, an aromatic group, —O—$R^{22}$, —CO—$R^{23}$, —CO—O—$R^{24}$, —N$R^{25}R^{26}$, —NHCO—$R^{27}$, —NH—CO—O—$R^{28}$, —SO$_2$—$R^{29}$ or —NH—SO$_2$—$R^{30}$, in which each of $R^{22}$, $R^{23}$, $R^{24}$, $R^{25}$, $R^{26}$, $R^{27}$, $R^{28}$, $R^{29}$ and $R^{30}$ independently is hydrogen, an aliphatic group or an aromatic group; each of $R^4$ and $R^5$ independently is hydrogen, an aliphatic group, an aromatic group, —CO—$R^{31}$ or —SO$_2$—$R^{32}$, in which each of $R^{31}$ and $R^{32}$ independently is an aliphatic group or an aromatic group; and $R^2$ and $R^3$, $R^3$ and $R^4$, $R^4$ and $R^5$, $R^5$ and $R^6$ or $R^6$ and $R^7$ can be combined with each other to form a ring.

17. The silver halide photographic material as claimed in claim 16, wherein the azomethine dye represented by the formula (II) is in the form of solid fine particles which are dispersed in the silver halide emulsion layer or in the non-light-sensitive hydrophilic colloidal layer.

18. The silver halide photographic material as claimed in claim 16, wherein Y is =O.

19. The silver halide photographic material as claimed in claim 16, wherein $R^1$ is hydrogen, an aliphatic group or an aromatic group.

20. The silver halide photographic material as claimed in claim 16, wherein each of $R^2$ and $R^7$ independently is hydrogen, an alkyl group or an alkoxy group; each of $R^3$ and $R^6$ is hydrogen; each of $R^4$ and $R^5$ independently is hydrogen, an alkyl group, or an aryl group; and $R^3$ and $R^4$ or $R^5$ and $R^6$ can be combined with each other to form a ring.

* * * * *